(12) United States Patent
Hanafusa et al.

(10) Patent No.: US 8,333,937 B2
(45) Date of Patent: Dec. 18, 2012

(54) DISPENSATION TIP, REACTION KIT USING THE SAME, AND DISPENSATION TIP DRIVE MECHANISM

(75) Inventors: Nobuhiro Hanafusa, Kyoto (JP); Atsushi Inami, Kyoto (JP); Tomoichi Takahashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 797 days.

(21) Appl. No.: 12/302,846

(22) PCT Filed: May 28, 2007

(86) PCT No.: PCT/JP2007/060807
§ 371 (c)(1),
(2), (4) Date: Nov. 28, 2008

(87) PCT Pub. No.: WO2007/139056
PCT Pub. Date: Dec. 6, 2007

(65) Prior Publication Data
US 2009/0191097 A1    Jul. 30, 2009

(30) Foreign Application Priority Data

Jun. 1, 2006  (JP) ................ 2006-153938
Jun. 13, 2006 (JP) ................ 2006-163044

(51) Int. Cl.
*B01L 3/14* (2006.01)
(52) U.S. Cl. ........ 422/550; 422/430; 422/501; 422/551; 422/552
(58) Field of Classification Search .......... 422/500–501, 422/509–525, 430, 547, 550, 551, 552, 553
See application file for complete search history.

(56) References Cited

U.S. PATENT DOCUMENTS

| 2,818,864 | A  | * | 1/1958 | Hudson .................. 604/415 |
| 4,830,832 | A  |   | 5/1989 | Arpagaus et al. |
| 6,943,035 | B1 | * | 9/2005 | Davies et al. .................. 436/180 |
| 2001/0018575 | A1 |   | 8/2001 | Lyza, Jr. |
| 2002/0090736 | A1 | * | 7/2002 | Ulin .............. 436/180 |

(Continued)

FOREIGN PATENT DOCUMENTS

EP     1 095 703 A1    5/2001

(Continued)

OTHER PUBLICATIONS

Notification of Reasons for Refusal for the Application No. 2006-153938 from Japan Patent Office mailed Jun. 15, 2010.

(Continued)

*Primary Examiner* — Jill Warden
*Assistant Examiner* — Dwayne K Handy
(74) *Attorney, Agent, or Firm* — Cheng Law Group, PLLC

(57) ABSTRACT

A surrounding environment and a solution to be dispensed are prevented from being polluted by aerosol inside a dispensation tip. A dispensation tip 20 is provided with a dispensation nozzle 19 attached to its distal end, a syringe having a hollow inner portion, that is connected to a proximal end of the dispensation nozzle 19, and a plunger 22 that is allowed to slide in the cylinder 21 of the syringe so that suction and discharge processes are carried out on the liquid by the dispensation nozzle 19. A separation member having airtightness for separating an inside of the nozzle 19 from the outside and flexibility for allowing the plunger 22 to freely slide is placed between the proximal end of the plunger 22 and the proximal end of the cylinder 21.

12 Claims, 24 Drawing Sheets

U.S. PATENT DOCUMENTS

| | | |
|---|---|---|
| 2003/0047761 A1 | 3/2003 | Yamamoto et al. |
| 2003/0072679 A1* | 4/2003 | Johnson et al. ............... 422/63 |
| 2003/0075557 A1 | 4/2003 | Deppe et al. |
| 2004/0096360 A1* | 5/2004 | Toi et al. ..................... 422/63 |
| 2005/0036919 A1* | 2/2005 | Hodson ...................... 422/100 |
| 2005/0106742 A1 | 5/2005 | Wahl |
| 2005/0161402 A1 | 7/2005 | Hanafusa et al. |

FOREIGN PATENT DOCUMENTS

| | | |
|---|---|---|
| JP | 53-131895 | 11/1978 |
| JP | 62-191049 A | 8/1987 |
| JP | 11-248717 A | 9/1999 |
| JP | 2001-121005 A | 5/2001 |
| JP | 2003-070456 A | 3/2003 |
| JP | 2003-511654 A | 3/2003 |
| JP | 2003-532120 A | 10/2003 |
| JP | 2004-061397 A | 2/2004 |
| JP | 2005-130851 A | 5/2005 |
| JP | 2005-214710 A | 8/2005 |
| JP | 2005-291954 A | 10/2005 |
| WO | WO-01/24933 A1 | 4/2001 |

OTHER PUBLICATIONS

Notification of Reasons for Refusal for the Application No. 2006-163044 from Japan Patent Office mailed Jun. 15, 2010.

International Search Report for the Application No. PCT/JP2007/060807 mailed Aug. 28, 2007.

* cited by examiner

DISPENSATION TIP, REACTION KIT USING THE SAME, AND DISPENSATION TIP DRIVE MECHANISM

TECHNICAL FIELD

The present invention relates to a dispensation tip suitable for carrying out various analyses such as biological analyses, biochemical analyses, and general chemical analyses in the fields of medical care, chemistry, and the like, and a reaction kit using such a dispensation tip, and also relates to a dispensation tip drive mechanism.

BACKGROUND ART

In biochemical analyses, general chemical analyses, and the like, micro multi-chamber devices have been used as small-size reaction devices. As such a device, for example, a microwell reaction plate such as a microtiter plate, which has a flat plate substrate with a plurality of wells formed on the surface of the substrate, is used.

As the dispensation tip, one which has a sharp tip and is hollow cone shaped has been used to be attached to a distal end of a suction and discharge nozzle used for dispensing a solution such as a sample and a reagent in these reaction devices.

DISCLOSURE OF THE INVENTION

Problems to be Solved by the Invention

However, upon dispensing a solution using the dispensation tip, components of the solution and reaction products tend to leak toward the suction and discharge nozzle side from the inside of the dispensation tip through aerosol to cause contamination and pollution in a surrounding environment. Further, a solution to be dispensed tends to be polluted through the aerosol inside the dispensation tip.

Therefore, an object of the present invention is to prevent the surrounding environment and the solution to be dispensed from being polluted by aerosol inside the dispensation tip.

Means for Solving the Problems

A dispensation tip in accordance with the present invention is provided with a dispensation nozzle being attached to a distal end thereof; a syringe being connected to a proximal end portion of the dispensation nozzle and having a hollow inner portion; a plunger sliding in a cylinder of the dispensation nozzle for sucking and discharging liquid through the dispensation nozzle; and a separation member being placed between a proximal end portion of the plunger and a proximal end portion of the cylinder, and the separation member having such airtightness as to separate an inside of the nozzle from outside and such flexibility as to allow the plunger to slide therein.

A dispensation tip drive mechanism in accordance with the present invention holds detachably a dispensation tip, which has an opening used for dispensation of liquid at a distal end thereof and a proximal end portion forming a cylinder with a plunger installed therein, and also drives the plunger. The dispensation tip drive mechanism includes: a tip holder for holding the proximal end portion of the dispensation tip from above so as to be detachably attached thereto, with the dispensation tip being disposed with the distal end thereof facing down; a sleeve being attached to the inside of the tip holder so as to be allowed to slide upward and downward; and a plunger holder attached to the inside of the sleeve so as to be allowed to slide upward and downward for holding detachably the upper end portion of the plunger from above. The plunger holder has a gap used for sandwiching the plunger at a distal end thereof, and is attached to the sleeve in such a manner that, when the plunger holder protrudes from the sleeve, the gap is opened wider than the size of the upper end portion of the plunger, while, when the plunger holder retreats relative to the sleeve, the gap is narrowed so as to grasp the upper end portion of the plunger, and by shifting the plunger holder upward and downward together with the sleeve, the plunger is allowed to slide upward and downward relative to the cylinder.

A structure may be proposed in which, by installing a first elastic member used for pressing the plunger holder in a retreating direction relative to the sleeve between the sleeve and the plunger holder, when the plunger holder is allowed to advance relative to the sleeve against the pressing force, the distal end of the plunger holder protrudes from the distal end of the sleeve, or another structure may be proposed in which, by installing a second elastic member used for pressing the sleeve in a retreating direction relative to the tip holder between the tip holder and the sleeve, with the second elastic member having an elastic force weaker than that of the first elastic member, the sleeve is allowed to shift upward and downward together with the plunger holder relative to the tip holder.

The tip holder may have a concave/convex portion on its outer surface so that the cylinder is attached thereto, with a shape to be fitted to the concave/convex portion on the outer surface of the tip holder being formed on the inner surface of the cylinder.

The dispensation tip to be applied to the dispensation tip drive mechanism of the present invention is not necessarily limited to a dispensation tip having a separation member of the present invention. However, upon dispensing a solution by using the dispensation tip, components of the solution and reaction products tend to leak toward the suction and discharge nozzle side from the inside of the dispensation tip through aerosol to cause contamination and pollution in a surrounding environment, and a solution to be dispensed tends to be polluted through the aerosol inside the dispensation tip. Therefore, the dispensation tip of the present invention may have a separation member having such airtightness as to separate the inside of the nozzle from the outside, and such flexibility as to allow the plunger to slide therein, that is placed between the upper portion of the plunger and the upper portion of the cylinder.

In a case of a conventional microwell reaction plate, since the surface of the reaction plate is exposed to ambient air during use, there is a possibility that foreign matter will enter a sample from the outside, and a reaction product will pollute the surrounding environment. Therefore, in order to prevent the entry of foreign matter from the outside into a reaction plate and the pollution of the surrounding environment, the reaction kit of the present invention includes: a reaction plate having a reaction container on the surface side thereof for causing a sample to react; a dispensation tip being placed above the surface side of the reaction plate and having an opening used for dispensation of liquid at its distal end and a proximal end portion that forms a cylinder with a plunger installed therein; and a cover for covering a plate upper-space on the surface of the reaction plate, and for movably supporting the dispensation tip, with the distal end being located inside the plate upper-space and the proximal end being located outside the plate upper-space.

Upon raising the plunger, a loop-shaped space, formed by the plunger, the cylinder and the separation member placed between the proximal end portion of the plunger and the proximal end portion of the cylinder, has a reduced pressure to sometimes cause failure to smoothly move the plunger and the separation member. Therefore, an air hole that communicates with the loop-shaped space formed by the cylinder, the plunger, and the separation member is preferably formed in the dispensation tip. In a case where the air hole is formed on the outside of the cover, since an effect of sealing the loop-shaped space from the outside by the separation member is reduced, the air hole is preferably formed on a portion of the cylinder proximal end portion placed inside the plate upper-space so that air that is present in the loop-shaped space can be exchanged with air that is present inside the plate upper-space covered with the cover.

Upon using this reaction kit, a sample should be introduced into the plate upper-space covered with the cover by using some step or other. Although the introducing step is not particularly limited, for example, a sample introducing section, which is used for injecting a sample into the plate upper-space from the outside through an opening formed on one portion of the cover so as to be tightly closed, may be further installed.

A reagent to be used for a reaction of the sample should also be introduced into the plate upper-space covered with the cover by using some step or other, and although the introducing step is not particularly limited, for example, the reagent may be introduced through the sample introducing section together with the sample, or the reagent, put into another container, may be introduced thereto, or it may be preliminarily housed in a reaction plate. In a form in which the reagent is preliminarily housed in a reaction plate, the reaction plate also has a reagent container housing the reagent, sealed by a film, on its surface side. The film that covers the reagent container to seal the reagent is a film that can be penetrated by the dispensation tip.

The plate upper-space on the surface side on the reaction plate is covered with the cover, and isolated from the outside, and the reaction of the sample is carried out in the plate upper-space. The detection of a reaction product after the reaction is carried out, with the reaction product being present inside the cover, without the necessity of taking the reaction product out of the cover. After the detection, the reaction kit is subjected to a waste disposal treatment, with the reaction product being left inside the cover. That is, the reaction kit is a disposable kit.

When the reaction kit is used for analyzing a gene, the reaction plate is preferably provided with a gene amplification section that causes a gene amplification reaction on its surface side. The gene amplification section is preferably formed into a shape that is suitable for controlling a temperature in a predetermined temperature cycle, and the reaction container may be formed into such a shape serving as the gene amplification section, or a gene amplification container may be installed separately from the reaction container. The gene amplification reaction includes a PCR method, a LAMP method and the like.

The analysis on the reaction product in the reaction container may be carried out inside the reaction container, or the reaction product may be transferred from the reaction container to another place on a reaction plate where the analysis may be carried out.

In a reaction kit where the analysis of the reaction product is carried out inside the reaction container, the reaction container is preferably made from a light-transmitting material so that optical measurements can be carried out from its bottom portion.

In a reaction kit where the analysis is carried out on the reaction product in another place to which it has been transferred from the reaction container, the reaction plate further includes on its surface side an analyzing section that analyzes the reaction product of the reaction container.

An example of such an analyzing section is an electrophoresis section for carrying out an electrophoretic separation on the reaction product.

Another example of such an analyzing section is a region in which, when a gene is contained in the reaction product, probes to react with the gene are arranged. Examples of such a probe region include DNA chips and hybridization regions.

An example of a structure that holds and movably supports the dispensation tip is a structure that holds and movably supports the dispensation tip using a material having airtight and flexible properties, such as a diaphragm and a film.

Another example of a structure that holds and movably supports the dispensation tip is a structure in which a cover is constituted by a cover main body that is integrally formed with the reaction plate and a cover plate that is placed on an upper portion of the surface side of the reaction plate, and held hermetically by a sealant so as to slide within a horizontal plane relative to the cover main body, while the dispensation tip is held hermetically on the cover plate by another sealant so as to be slidable in a vertical direction.

The reaction kit of the present invention is suitably used for carrying out various measurements on reactions, such as chemical reactions and biochemical reactions. Not particularly limited, the sample to be measured by using the reaction kit of the present invention includes various samples, such as chemical substances, biological samples, and samples derived from organisms.

Effects of the Invention

In the dispensation tip of the present invention, the separation member that has such airtightness as to separate an inside of the nozzle from outside, and such flexibility as to allow the plunger to slide therein is placed between the proximal end portion of the plunger and the proximal end portion of the cylinder of the syringe. Therefore, even when the plunger is allowed to slide, it is possible to suppress components of the solution and reaction products from leaking outside the separation member of the plunger and the cylinder through aerosol to consequently prevent contamination and pollution in a surrounding environment.

Moreover, when the air hole that communicates with the loop-shaped space formed by the cylinder, the plunger, and the separation member is formed, it becomes possible to prevent the loop-shaped space from having a reduced pressure upon raising the plunger so that the plunger and the separation member are allowed to move smoothly, thereby making it possible to carry out an accurate analysis.

Since the reaction kit of the present invention is used with the plate upper-space on the surface side of the reaction plate being covered with the cover, it is possible to prevent foreign matter from entering a sample from the outside, and also to prevent the reaction products from polluting a surrounding environment. Further, since the dispensation tip of the present invention makes it possible to completely close the inside of the dispensation nozzle from the outside space by using a simple mechanism, a size of the reaction container can be reduced.

In a case where an air hole that communicates with a loop-shaped space formed by the cylinder, the plunger, and the separation member is formed, it becomes possible to prevent the loop-shaped space from having a reduced pressure upon raising the plunger so that the plunger and the separation member are allowed to move smoothly, thereby making it possible to carry out an accurate analysis.

In a case where an air hole is formed on a portion of the cylinder proximal end portion placed inside the plate upper-space, air that is present in the loop-shaped space of the cylinder in a completely closed state from the outside space can be exchanged with air that is present inside the plate upper-space so that it becomes possible to prevent pollution in a surrounding environment and also to reduce a size of equipment.

When a sample introducing section is further installed, it becomes possible to easily carry out a sample introducing process into the plate upper-space covered with the cover.

In a case where a reagent used for a reaction with the sample is introduced through a sample introducing section together with the sample, the general purpose utility of the reaction kit is improved. In contrast, in a case where the reagent is preliminarily housed in the reaction plate, since it is not necessary to prepare a reagent on the equipment side that carries out treatments on the reaction kit, the processing equipment can be simplified.

In a case where the dispensation tip is provided with a syringe that is operated from the outside of the cover, it is not necessary to install the nozzle mechanism separately.

In a case where the reaction plate is further provided with a gene amplification section, even a sample containing a trace amount of a gene to be measured may be used by amplifying the gene through a gene amplification reaction such as a PCR method and a LAMP method. Thus, its analyzing precision can be improved.

In a case where the dispensation tip is provided with a filter inside its distal end, it is possible to prevent a foreign matter from entering therein from the outside through the dispensation tip and also to prevent the reaction product from polluting a surrounding environment through the dispensation tip even if the dispensation tip is not provided with a syringe.

Upon carrying out a gene amplification reaction, a problem arises in which another DNA or the like enter the sample from the outside. Moreover, another problem arises in which the amplified gene contaminates another sample. In the present invention, the gene amplification reaction is also carried out in the closed plate upper-space, and after the completion of the analysis, since the disposal treatment is carried out with the sample being closed inside the plate upper-space, it is possible to prevent contamination caused from the outside and also to prevent another sample from being polluted.

In a case where the analysis of the reaction product in the reaction container is carried out in the reaction container, or when the analysis thereof is carried out in an electrophoresis section placed separately from the reaction container, or in a probe area that reacts with the gene, the kinds of samples to be dealt with can be widened.

In a case where the structure for holding and movably supporting the dispensation tip is achieved by using a material having airtightness and flexibility, or when the cover is made of a cover main body and a cover plate so that the dispensation tip can be movably supported by the sliding process of the cover plate relative to the cover main body as well as by the sliding process of the dispensation tip relative to the cover plate, it becomes possible to achieve a structure for holding and movably supporting the dispensation tip by using a simple structure.

The dispensation tip drive mechanism of the present invention includes a tip holder, a sleeve and a plunger holder. By the gap on the distal end of the plunger holder, the plunger holder protrudes from the sleeve, grasping the upper end of the plunger, it is possible to hold and drive the dispensation tip.

In a case where elastic members are installed between the sleeve and the plunger holder as well as between the tip holder and the sleeve, since the moving process is carried out by utilizing the force of the elastic members, the dispensation tip can be easily attached, and the plunger is also allowed to slide easily.

When a concave/convex shape is formed on a contact face between the tip holder and the cylinder, the dispensation tip can be easily attached to the drive mechanism.

Figure 1:
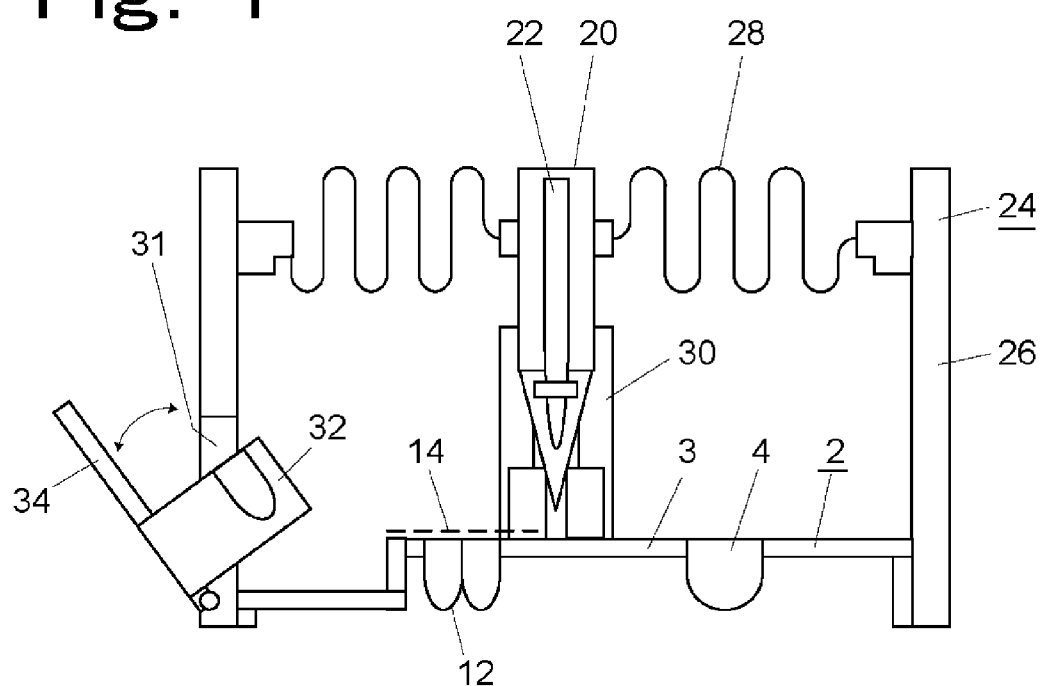
FIG. 1 is a vertical sectional view of one embodiment of a reaction kit.

DESCRIPTION OF THE REFERENCE SYMBOLS 2, 2a, 2b, 2c Reaction plate
3 Substrate
4 Reaction container
12 Reagent container
14 Film
19 Dispensation nozzle
20 Dispensation tip
21 Cylinder
22 Plunger
23 Filter
24 Cover
26 Cover main body
28 Bellows film
32, 32a Sample container
36a Tip holder
36b Plunger holder
64, 64a, 71 Cover plate
66, 68, 72 Sealant
90 Drive mechanism
92a, 94a Coil screw
93 Sleeve
95 Loop-shaped space
96 Separation member
98a, 98b Packing
99 Air hole
100, 110, 120 DNA chip
106 Electrode
102 Electrophoretic separation channel

BEST MODE FOR CARRYING OUT THE INVENTION

Figure 2:
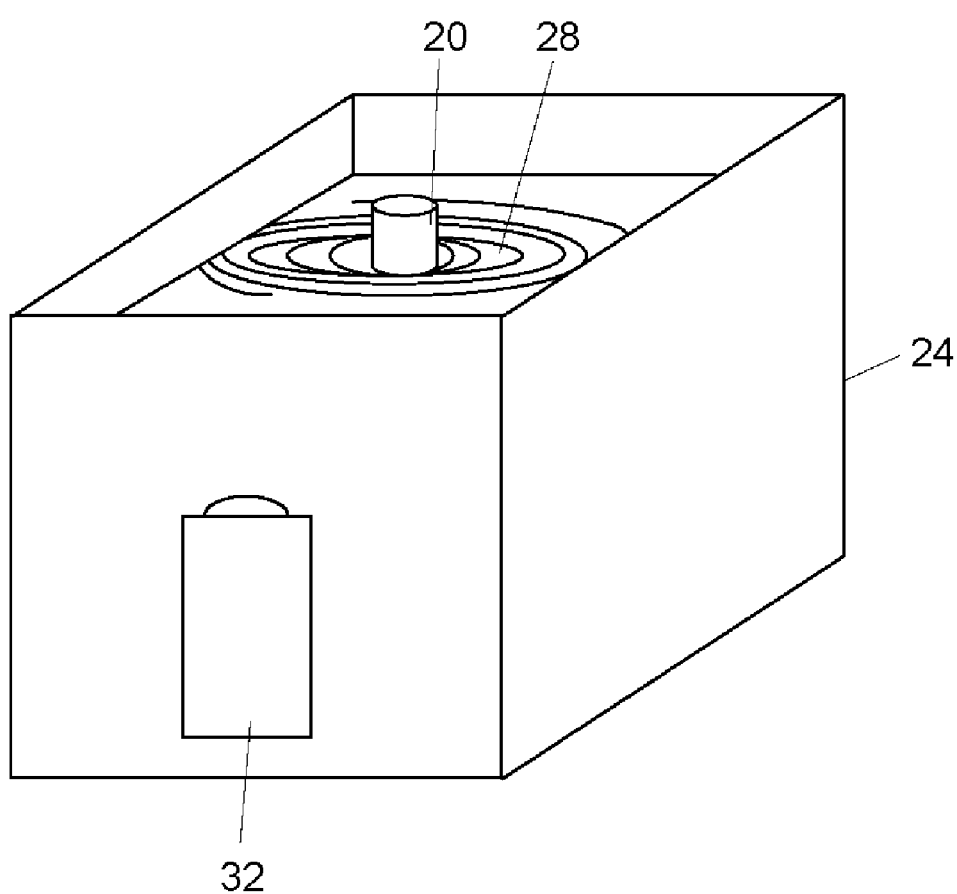
FIG. 2 is an outside perspective view of the embodiment.

FIG. 1 shows a vertical sectional view of a reaction kit according to one embodiment, and FIG. 2 is a perspective view of the embodiment. As shown in FIG. 1, the reaction plate 2 is provided with a reaction container 4 for causing a reaction on a sample and a reagent container 12 that houses a reagent used for causing the reaction in the sample and is sealed by a film 14, on the surface side of a substrate 3.

The reaction container 4 is provided as a recess in the top surface of the substrate 3. In a case where the reaction container 4 is intended for reaction carried out under externally-controlled temperature conditions, a part of the reaction container 4 subjected to temperature control preferably has a small thickness to enhance heat conductivity.

Each of the reagent containers 12 is also provided as a recess in the top surface of the substrate 3, and contains a reagent to be used for reaction, and is covered with the film 14 through which the dispensation tip 20 (which will be described later) can pass. Examples of such a film 14 include an aluminum foil, and a laminated film having an aluminum film and a resin film such as a PET (polyethylene terephthalate) film. The film 14 is attached by welding or adhesion so as not to be easily detached.

If necessary, a mixing chamber for mixing a sample with a reagent may be provided as a recess in the top surface of the substrate 3. Further, such a mixing chamber may be covered with the film 14 with its recess being empty.

The reaction container 4 may be used as a detection chamber for detecting a reaction product formed in the reaction container 4. In this case, detection of a reaction product can be carried out by, for example, means for externally irradiating the reaction container 4 with light. Alternatively, a detection chamber may be provided separately from the reaction container 4. For example, in a case where a plurality of detection chambers are provided separately from the reaction container 4, the detection chambers may previously contain different reagents for detecting the state of a reaction mixture obtained by the reaction of a sample with a reagent, and the reaction mixture is dispensed into the detection chambers by the dispensation tip 20. The opening of such a detection chamber may be covered with a film through which the dispensation tip 20 can pass. As in the case of the film 14, examples of the film for covering the detection chamber include an aluminum foil and a laminated film having an aluminum film and a resin film such as a PET film, and the film can be attached by welding or adhesion so as not to be easily detached.

The material of the substrate 3 having the reaction container 4 is not particularly limited, but is preferably cheaply available because the reaction kit is disposable. Preferred examples of such a material include resin materials such as polypropylene and polycarbonate. In a case where the reaction kit is designed to allow a reaction product to be detected by absorbance, fluorescence, chemiluminescence, or bioluminescence in the reaction container 4 or a detection chamber provided separately from the reaction container 4, the substrate 3 is preferably made of an optically-transparent resin so that the reaction product can be optically detected from the bottom surface side of the substrate 3. Particularly, in a case where a reaction product is detected by fluorescence, the substrate 3 is preferably made of a low self-fluorescence (i.e., the amount of fluorescence emitted from a material itself is small) and an optically-transparent resin such as polycarbonate. The thickness of the substrate 2 is in the range of 0.3 to 4 mm, preferably in the range of 1 to 2 mm. From the viewpoint of low self-fluorescence, the thickness of the substrate 3 is preferably small.

The dispensation tip 20 is arranged above the top surface of the reaction plate 2. The dispensation tip 20 is used to dispense a sample and a reagent. Further, in a case where the reaction plate 2 has a detection chamber provided separately from the reaction container 4, the dispensation tip 20 is also used to dispense a reaction mixture obtained by reacting a sample with a reagent into the detection chamber. The dispensation tip 20 has a plunger 22, and the plunger 22 is driven from the outside of a cover 24 to carry out dispensation operation.

The following description will discuss a dispensation tip 20 and a drive mechanism 90 that holds and drives the tip.

Figure 3:
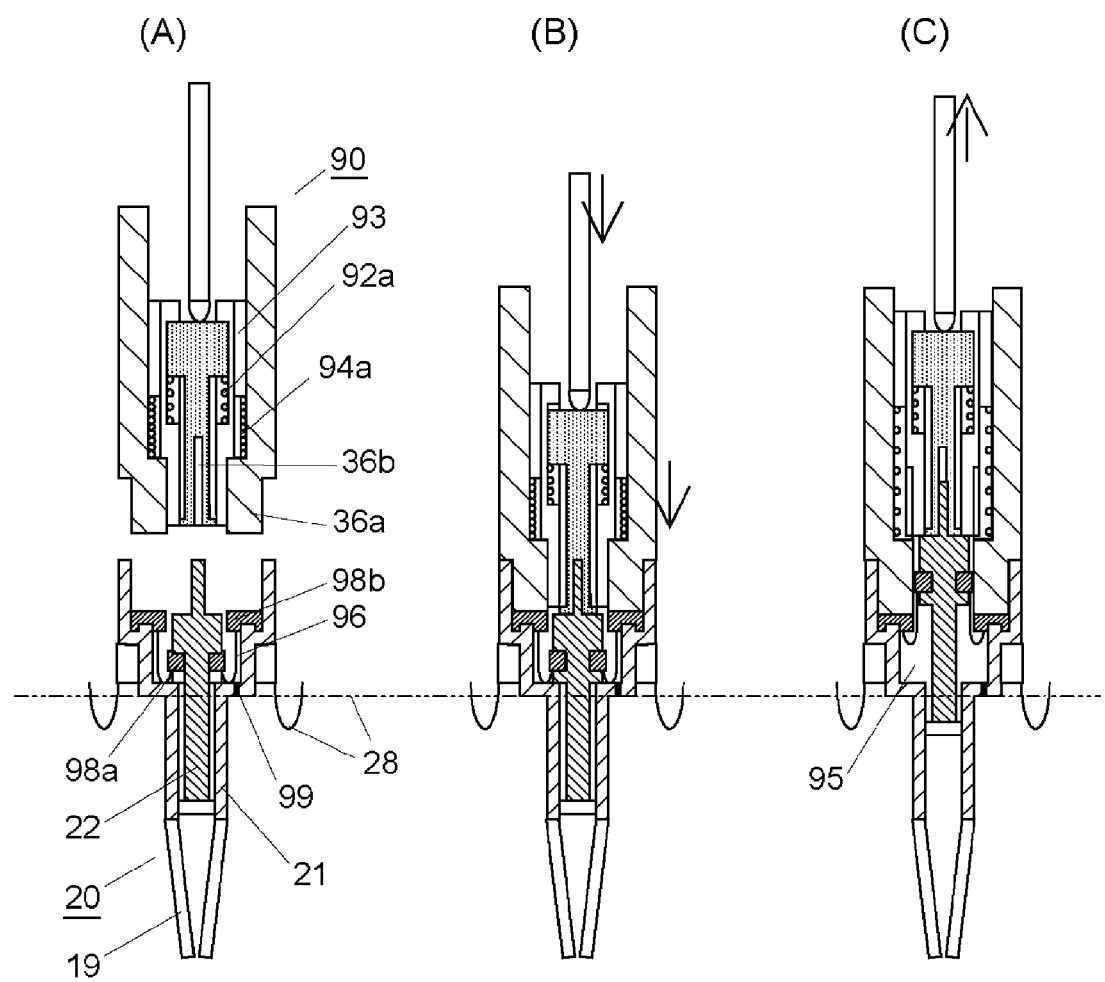
FIG. 3 shows a dispensation tip 20 and a drive mechanism that holds and drives the tip in a cross-sectional view; (A) is a state prior to attaching the drive mechanism to the dispensation tip, (B) is a state in which the drive mechanism is attached to the dispensation tip, and (C) is a state in which a plunger inside the dispensation tip is raised.

FIG. 3 shows the dispensation tip 20 and the drive mechanism that holds and drives the tip; moreover, FIG. 3A is a cross-sectional view showing a state prior to attaching the drive mechanism to the dispensation tip, FIG. 3B is a cross-sectional view showing a state in which the drive mechanism is attached to the dispensation tip, and FIG. 3C is a cross-sectional view showing a state in which a plunger 22 inside the dispensation tip is raised.

The dispensation tip 20 includes a dispensation nozzle 19 that carries out suction and discharge processes on liquid through its distal end, a cylinder 21 having a hollow inner portion that is connected to the top portion of the dispensation nozzle 19, and a plunger 22 that is allowed to slide upward and downward in the cylinder 21 so that the suction and discharge processes are carried out on the liquid. A syringe is a device in which the cylinder 21 and the plunger 22 that slides the inside of the cylinder 21 upward and downward are combined.

The drive mechanism 90, which can hold the plunger 22 and the dispensation tip 20 separately, includes a plunger holder 36b that is positioned coaxially on the plunger 22, a sleeve 93 that is placed on the periphery of the plunger holder 36b and can shift upward and downward relative to the plunger holder 36b (in directions parallel to the axis), and a tip holder 36a that is placed outside the sleeve 93 and can shift upward and downward relative to the sleeve 93 (in directions parallel to the axis).

The plunger holder 36b has a gap used for sandwiching the plunger 22 at its distal end, and is attached to the sleeve 93 in such a manner that the gap is allowed to open wider than the size of the upper end of the plunger 22, when the plunger holder 36b protrudes from the sleeve 93, while the gap is narrowed when the plunger holder 36b retreats toward the sleeve, so as to grasp the upper end of the plunger 22.

By shifting the plunger holder 36b upward and downward together with the sleeve 93, the plunger 22 is allowed to slide upward and downward relative to the cylinder 21.

A first elastic member 92a, which presses the plunger holder 36b in the retreating direction relative to the sleeve 93, is placed between the sleeve 93 and the plunger holder 36b so that, when the plunger holder 36b is made to advance against the pressing force relative to the sleeve 93, the distal end of the plunger holder 36b is allowed to protrude from the distal end of the sleeve 93.

A second elastic member 94b, which presses the sleeve 93 in the retreating direction relative to the tip holder 36a, is placed between the tip holder 36a and the sleeve 93, and since the elastic force of this elastic member is made weaker than that of the first elastic member, the sleeve 93 is allowed to shift upward and downward together with the plunger holder 36b relative to the tip holder 36a.

The distal end of the tip holder 36a is designed so that the cylinder 21 is attached thereto, through friction or by a securing member or the like. For example, a concave/convex portion is formed on the outer surface of the tip holder 36a, and a shape to be fitted to the concave/convex portion may be formed on the inner surface of the cylinder 21.

A separation member 96 is formed in a manner so as to connect a packing 98a formed on the upper portion of the plunger 22 to a packing 98b formed on the upper portion of the cylinder 21. A material having airtight and flexible properties is preferably used as the material for the separation member 96, and for example, a diaphragm and a thin film may be used. Silicone rubber, ethylene propylene rubber (EPDM) or butyl rubber may be used as the material having flexibility.

A loop-shaped space 95 is formed by the separation member 96, the cylinder 21 and the plunger 22. The volume of this loop-shaped space 95 is varied by the shift of the plunger 22. In order to exchange air between the loop-shaped space 95 and a plate upper-space covered with a bellows film 28, an air hole 99 is formed on a portion of the proximal end of the cylinder 21 located inside the plate upper-space.

Figure 4:
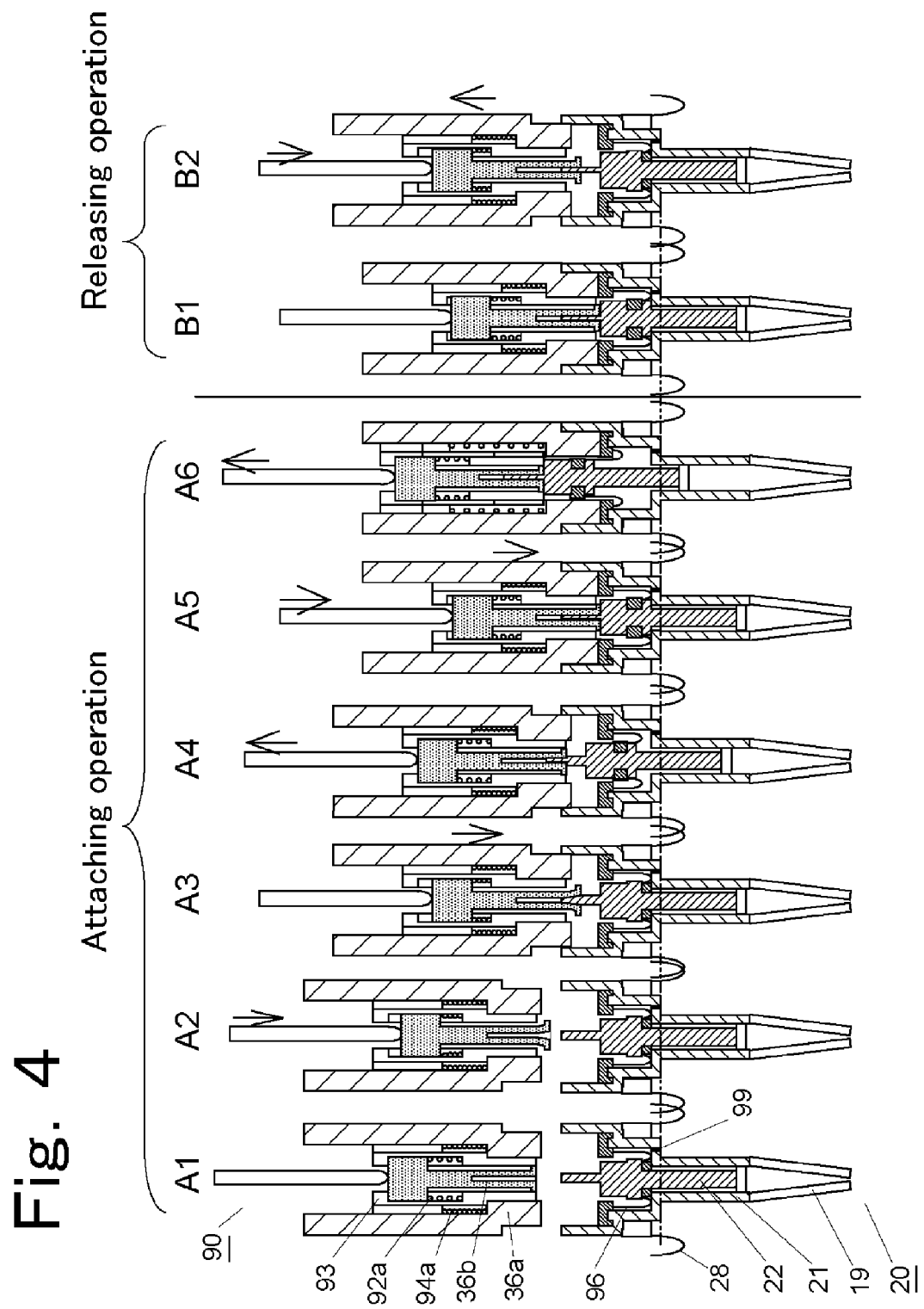
FIG. 4 is a vertical sectional view that shows attaching operations A1 to A6 in which the dispensation tip 20 is attached to a drive mechanism 90 and releasing operations B1 and B2 in which the drive mechanism 90 releases the dispensation tip 20 in the embodiment.

FIG. 4 is a vertical sectional view that shows attaching operations A1 to A6 in which the dispensation tip 20 is attached to a drive mechanism 90 and releasing operations B1 and B2 in which the drive mechanism 90 releases the dispensation tip 20.

Here, A1 indicates an initial state before the dispensation tip 20 is attached to the drive mechanism 90, and the plunger holder 36b is housed inside the sleeve 93. A gap like a tip of an automatic pencil is formed on the distal end of the plunger holder 36b so that, upon protrusion of the plunger holder 36b from the sleeve 93, the gap becomes wider to allow the outer diameter of the distal end of the plunger holder 36b to open wider than the size of the upper end of the plunger 22.

Moreover, A2 indicates a state in which the plunger holder 36b is pressed downward, and the distal end of the plunger holder 36b protruding from the inside of the sleeve 93 is widened to a size that sufficiently allows the upper end of the plunger 22 to be grasped. A coil spring 92a serving as an elastic member is shrunk by pressing down the plunger holder 36b.

Here, A3 indicates a state in which the upper end of the plunger 22 is temporarily fitted to the plunger holder 36b, with the size of its distal end being widened. Since both of the coil springs 92a and 94a are shrunk, the tip holder 36a is also lowered together with the plunger holder 36b so that the tip holder 36a is brought in contact with the cylinder 21 to be ready for the attaching process.

Moreover, A4 indicates a state in which the plunger holder 36b to which the plunger 22 is temporarily fitted is extended upward by an expanding elastic force of the coil spring 92a; thus, the gap of the distal end of the plunger holder 36b is narrowed sufficiently to grasp the plunger 22 so that the distal end of the plunger 22 is attached to the sleeve 93.

Furthermore, A5 indicates a state in which, while the plunger holder 36b is being pressed downward, the tip holder 36a is also pressed downward. The gap, formed on the distal end of the plunger holder 36b, is allowed to protrude outside the sleeve 93, and consequently widened, so that it is allowed to hold a portion of the plunger 22 with a predetermined length from its upper end. The distal end of the tip holder 36a is shoved into the cylinder 21 to be finally attached to the cylinder 21. The tip holder 36a and the cylinder 21 are fitted to each other through, for example, concave/convex portions, and secured to each other.

A6 indicates a state in which, after the attaching process, the plunger 22 is made to slide upward and downward by the coil spring 94a. When the plunger 22 is raised by a fixed amount, a predetermined amount of liquid is sampled, and when the plunger 22 is lowered by a fixed amount, a predetermined amount of liquid is discharged.

B1 indicates a state in which the drive mechanism is attached to the dispensation tip 20.

B2 indicates a state in which the drive mechanism 90 is detached from the dispensation tip 20. A force pressing downward is applied to the plunger holder 36b, while an upward raising force is applied to the tip holder 36a. The size of the distal end of the plunger holder 36b is widened to a size that releases the plunger 22 so that the drive mechanism 90 releases the dispensation tip 20. Moreover, the cylinder 21 is released from the tip holder 36a.

Figure 24:
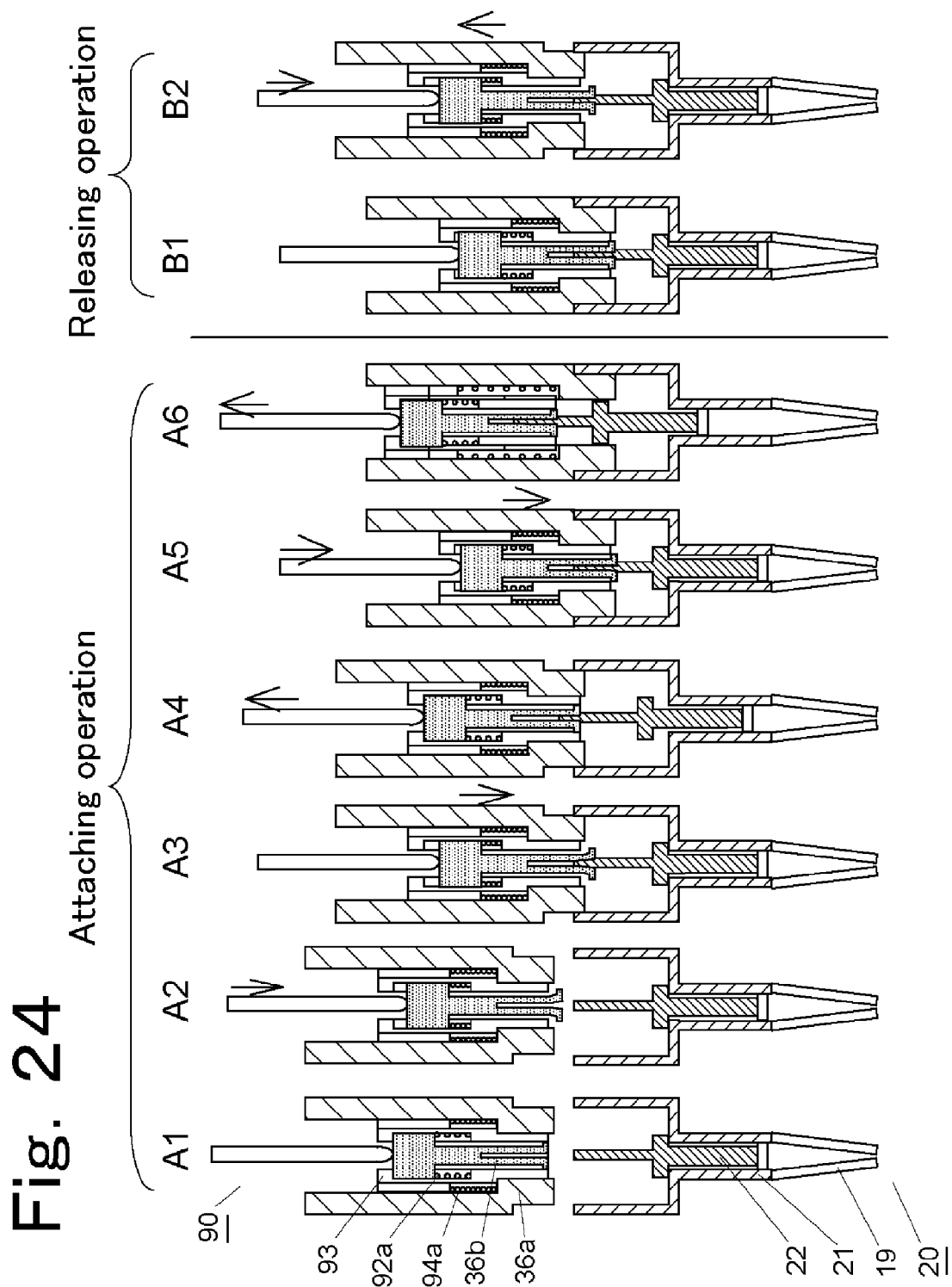
FIG. 24 is a vertical sectional view that shows attaching operations A1 to A6 in which another dispensation tip is attached to a drive mechanism and releasing operations B1 and B2 in which the drive mechanism releases the corresponding dispensation tip.

The dispensation tip to be handled in the dispensation tip drive mechanism of the present invention is not limited to the mechanism provided with the separation member 96 as shown in FIG. 3, and also includes a dispensation tip without the separation member 96. The operations of the structure using a dispensation tip without the separation member 96 are shown in FIG. 24 in a manner corresponding to FIG. 4. The operations thereof are the same as those shown in FIG. 4.

Next, the cover 24 will be described.

The cover 24 is provided so as to cover a space above the top surface of the reaction plate 2. The cover 24 includes a cover main body 26 for covering the periphery of the reaction plate 2 and a bellows film 28 for covering the top of the reaction plate 2 so that a space above the top surface of the reaction plate 2 is cut off from the outside. The cover main body 26 is provided integrally with the reaction plate 2 by fixing the lower end of the cover main body 26 to the reaction plate 2 or by using a sealant provided between the lower end of the cover main body 26 and the reaction plate 2, and has stiffness to maintain the shape of the cover 24. The bellows film 28 is formed from a flexible diaphragm or a flexible film, and movably holds the dispensation tip 20 so that a distal end thereof is located inside a space covered with the cover 24 and a proximal end thereof is located outside the space covered with the cover 24.

The material of the cover 24 is not particularly limited as long as it can cover a space above the top surface of the reaction plate 2 while keeping the reaction kit hermetically sealed. However, the cover 24 is preferably made of a cheaply-available material because the reaction kit is disposable. Preferred examples of a material for forming the cover main body 26 include resin materials such as polypropylene and polycarbonate, and preferred examples of a material for forming the bellows film 28 include Nylon®, polyvinyl chloride, and rubber materials such as silicone rubber and the like.

A holding member 30 for holding the dispensation tip 20 before and after its use is provided on the cover main body 26 or the substrate 3. When used for dispensation operation, the dispensation tip 20 is detached from the holding member 30 so as to be freely moved over the top surface of the reaction plate 2.

The cover main body 26 has an opening 31 for supplying a sample onto the reaction plate 2 from the outside of the cover 24. Further, a sample container 32 is openably and closably attached to the opening 31. The sample container 32 has a recess for receiving a sample, and the recess has an opening formed in the top surface of the sample container 32. After a sample is injected into the recess and is then placed inside the cover 24, the opening 31 is hermetically sealed by bringing a plate 34 holding the sample container 32 into intimate contact with the cover main body 26 using a pressure-sensitive adhesive applied onto the inner surface of the plate 34 or by engaging the plate 34 with the cover main body 26 with a sealant interposed therebetween. That is, the opening 31 is an opening hermetically sealable.

The reaction kit is disposable, and is therefore entirely disposed of without removing the cover 24 from the reaction plate 2 after the completion of analysis of one sample.

Hereinafter, the operation of analyzing a sample with the reaction kit of this embodiment will be described.

Prior to analysis, a sample is injected into the sample container 32 through the opening 31, and then the opening 31 is closed by the sample container 32, and therefore the sample container 32 is fixed to the cover main body 26. As a result, the sample is placed in a space covered with the cover 24 of the reaction kit and is cut off from the outside.

Figure 5:
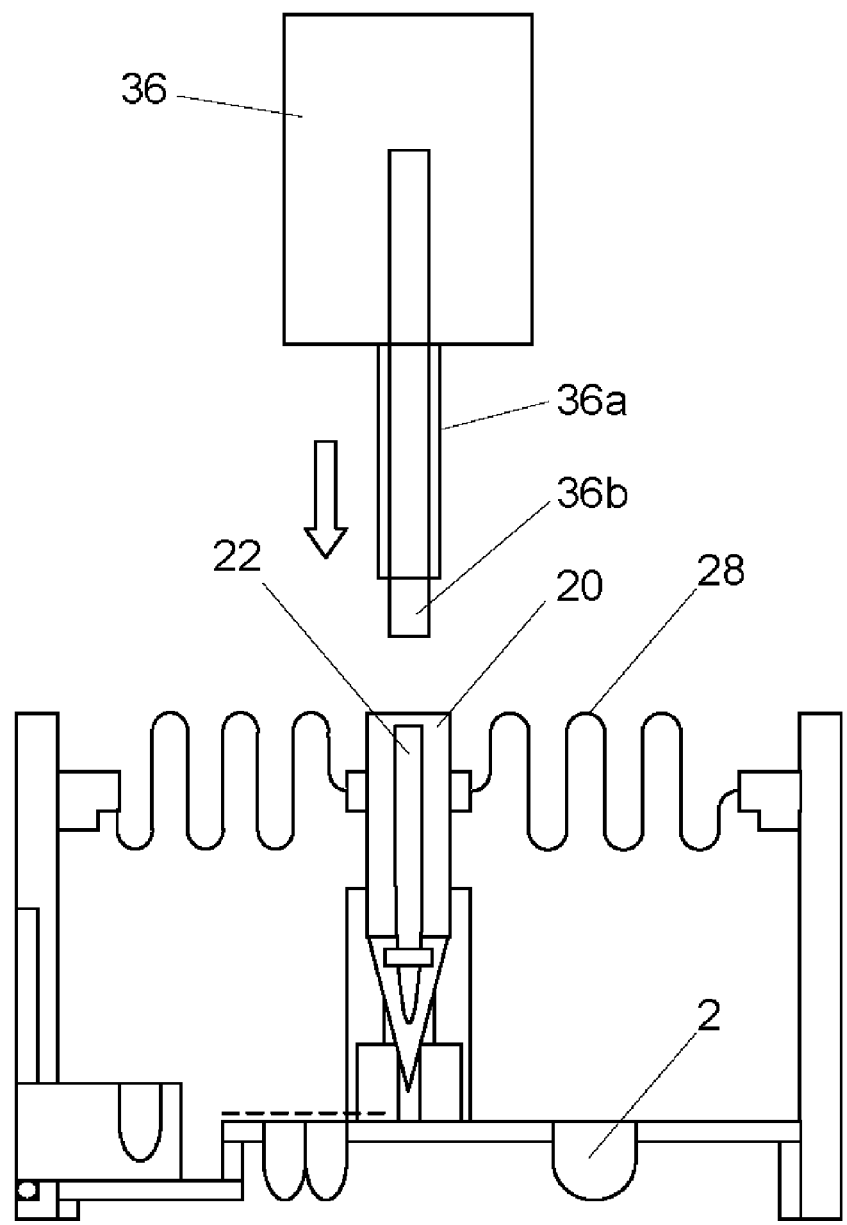
FIG. 5 is a vertical sectional view that shows a state in which a sample is introduced in the embodiment.
Figure 6:
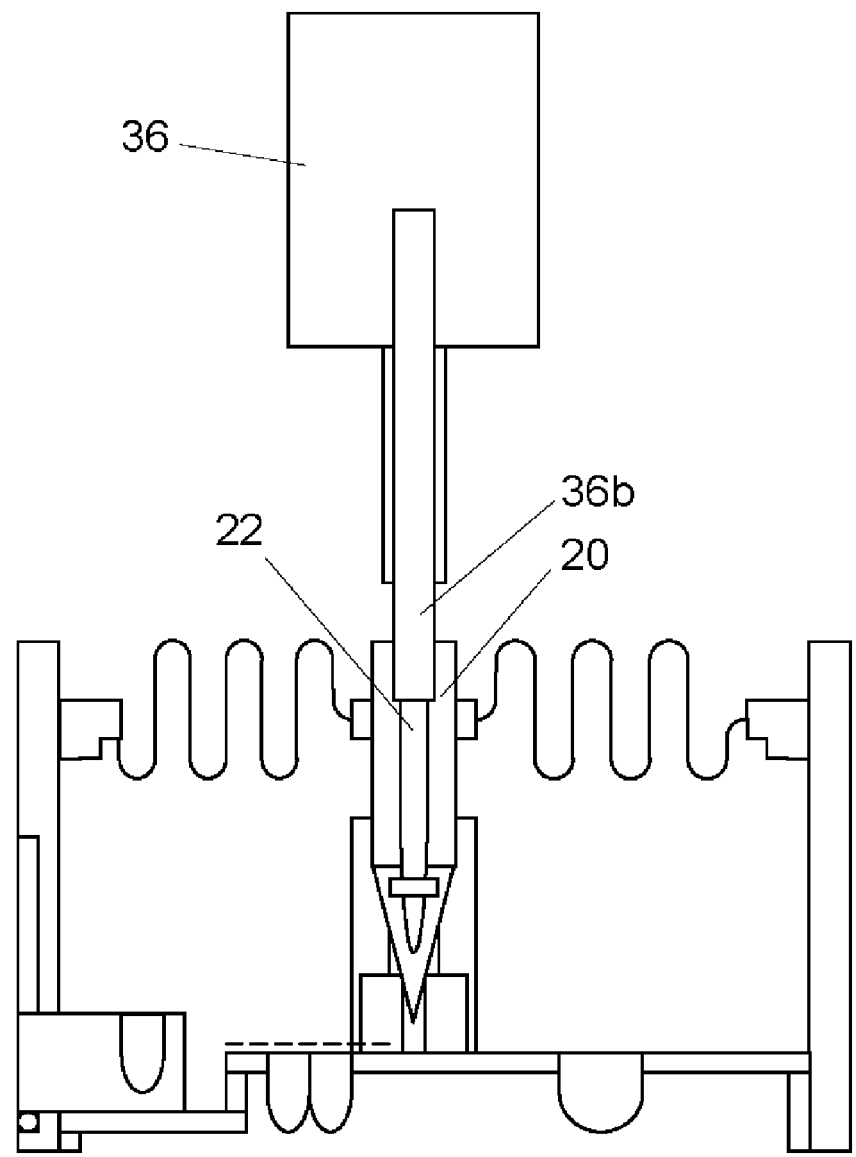
FIG. 6 is a vertical sectional view showing a state after a syringe drive section of a drive unit is engaged with a plunger of a syringe in the embodiment.
Figure 7:
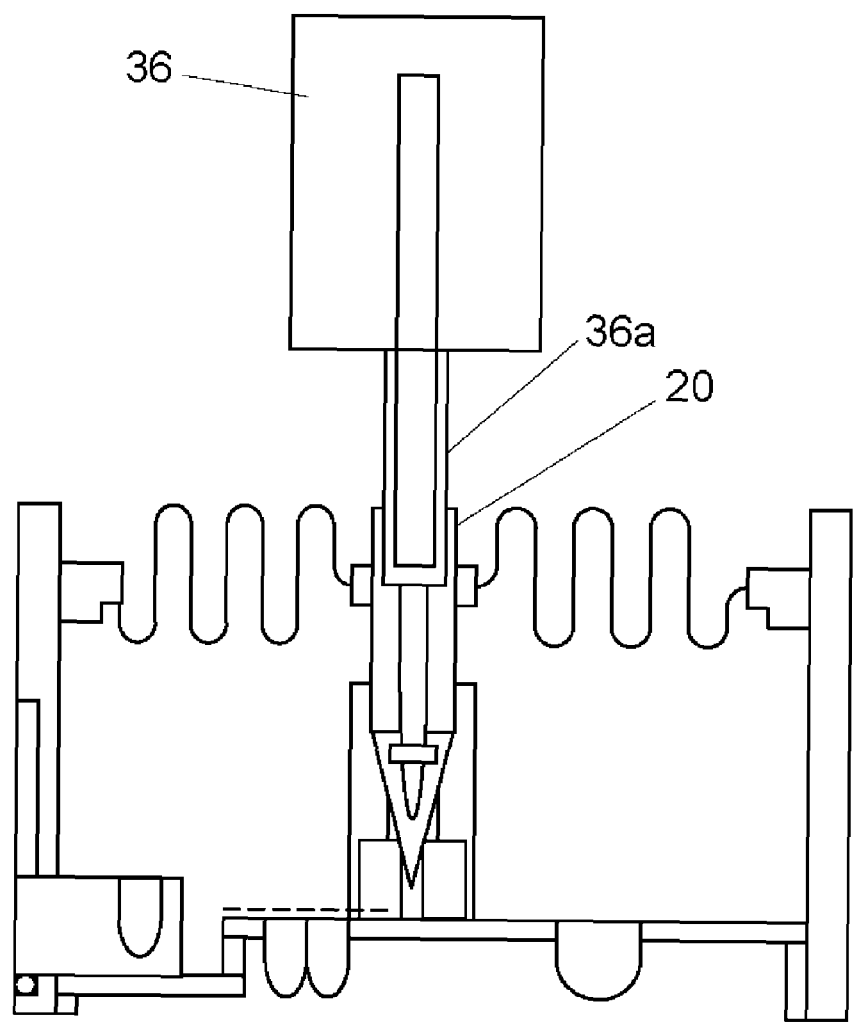
FIG. 7 is a vertical sectional view showing a state after a tip holding section of the drive unit is engaged with the dispensation tip in the embodiment.

After the sample is introduced into the reaction kit, as shown in FIG. 5, engagement of a drive unit 36 with the dispensation tip 20 and the cylinder 21 is allowed to start. First, as shown in FIG. 6, a plunger holder 36b is moved down to be engaged with a plunger 22 of the syringe. Then, as shown in FIG. 7, a tip holder 36a is also moved down to be press-fitted to the dispensation tip 20 so that the dispensation tip 20 is held by the tip holder 36a.

Figure 8:
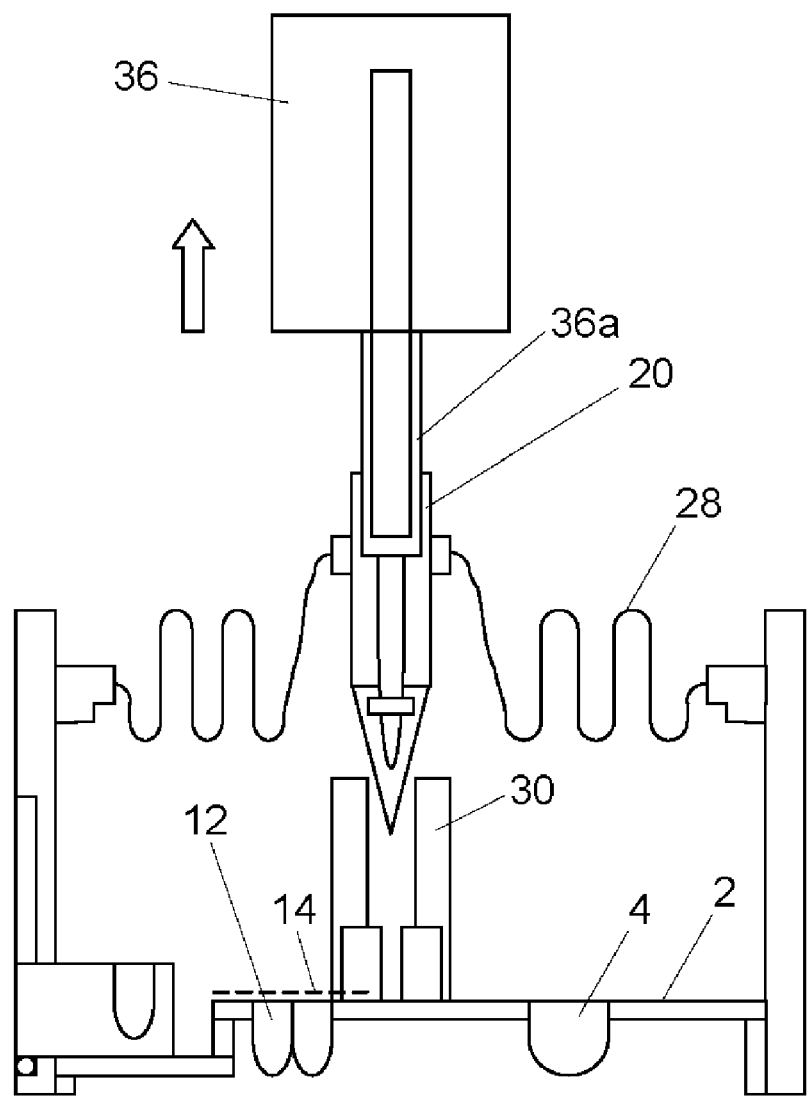
FIG. 8 is a vertical sectional view showing a state after the dispensation tip is detached from the holding section in the embodiment.

Next, as shown in FIG. 8, the dispensation tip 20 is detached from the holding section 30. In this way, the dispensation tip 20 becomes able to be freely moved by the bellows film 28 with its distal end being cut off from the outside.

The dispensation tip 20 is moved to the sample in the sample container 32, and then the sample is dispensed into the reaction container 4 by the dispensation tip 20. Next, the dispensation tip 20 is moved to the reagent container 12, and the distal end of the dispensation tip 20 is passed through the film 14 to take a reagent from the reagent container 12. The regent is then dispensed into the reaction container 4 by the dispensation tip 20 to react the sample with the reagent. If necessary, the reaction container 4 is brought into contact with an external heat source during the reaction to adjust the temperature of the reaction container 4 to a predetermined temperature.

During or after the reaction, detection of a reaction product is carried out. In this case, it is assumed that a reaction product contained in the reaction container 4 is optically detected from the outside of the reaction plate 2. Therefore, a detection unit is arranged below the reaction container 4 to detect a reaction product by optical means or other means.

As described in the above embodiment, the reaction plate 2 of the reaction kit has reagent containers 12, but the reagent containers 12 can be omitted from the reaction plate 2. In this case, both a sample and a reagent may be injected into the sample container 32 to introduce them into the reaction kit, or another container not shown may be used to introduce a reagent into the reaction kit.

Figure 9:
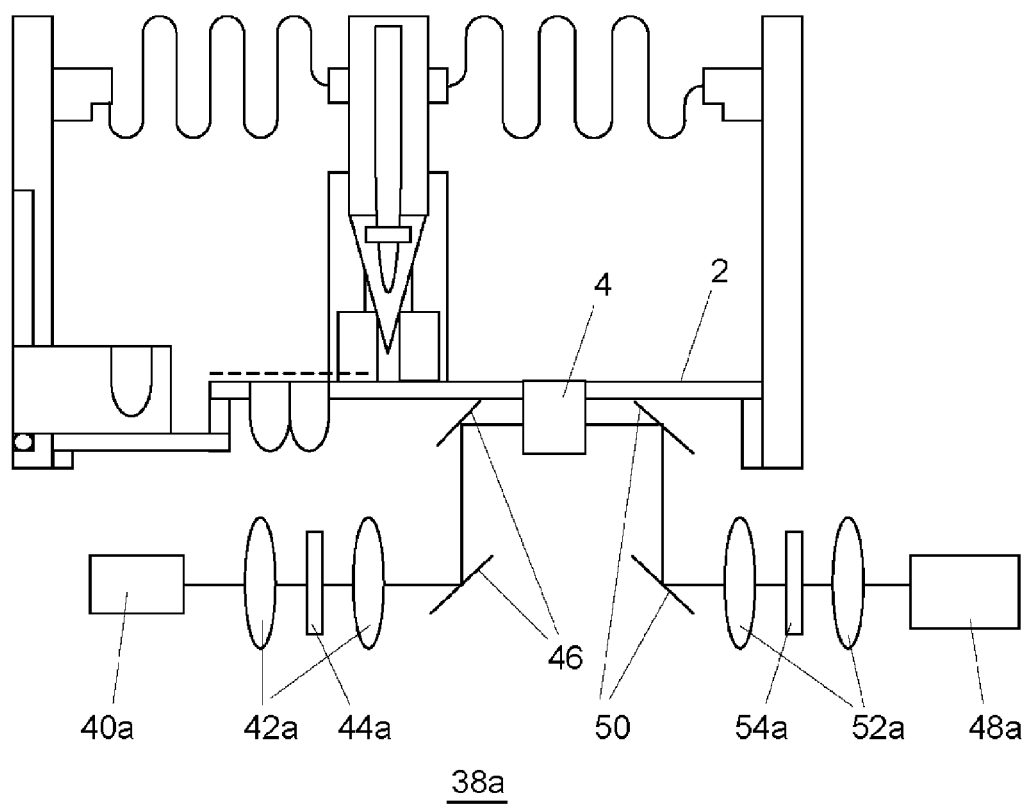
FIG. 9 is a vertical sectional view showing a first embodiment of a detection unit used for the detection of a reaction product in the reaction kit of the present invention.
Figure 10:
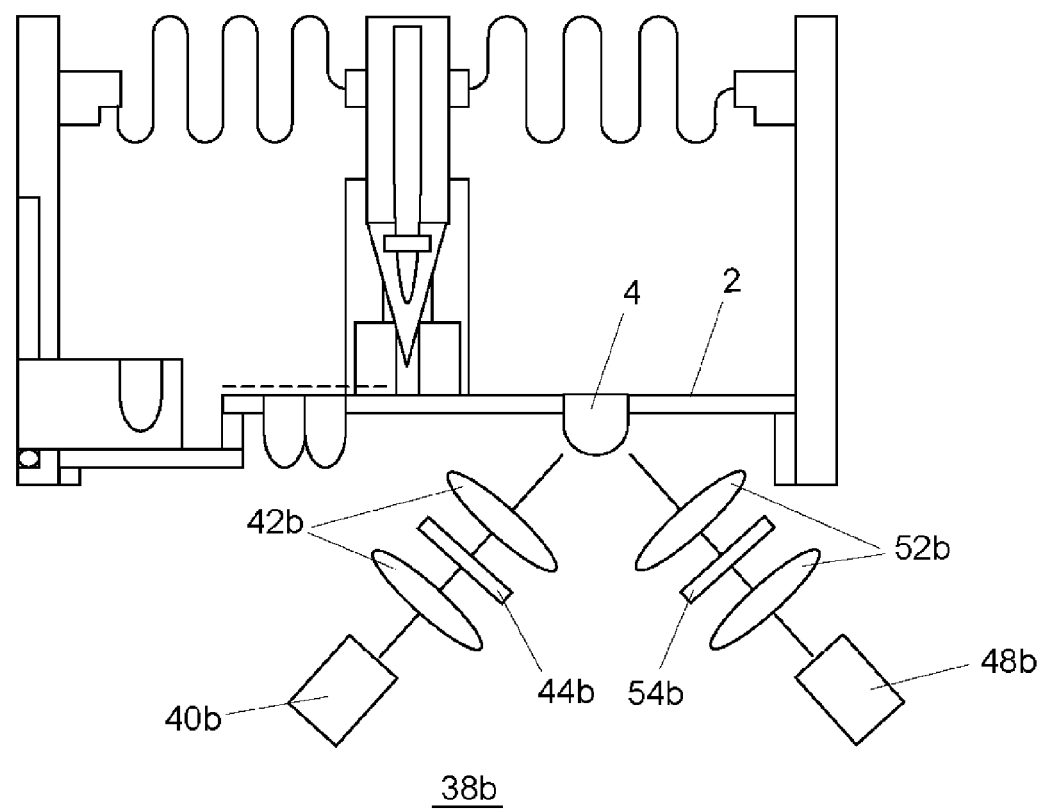
FIG. 10 is a vertical sectional view showing a second embodiment of the detection unit used for the detection of a reaction product in the reaction kit of the present invention.
Figure 11:
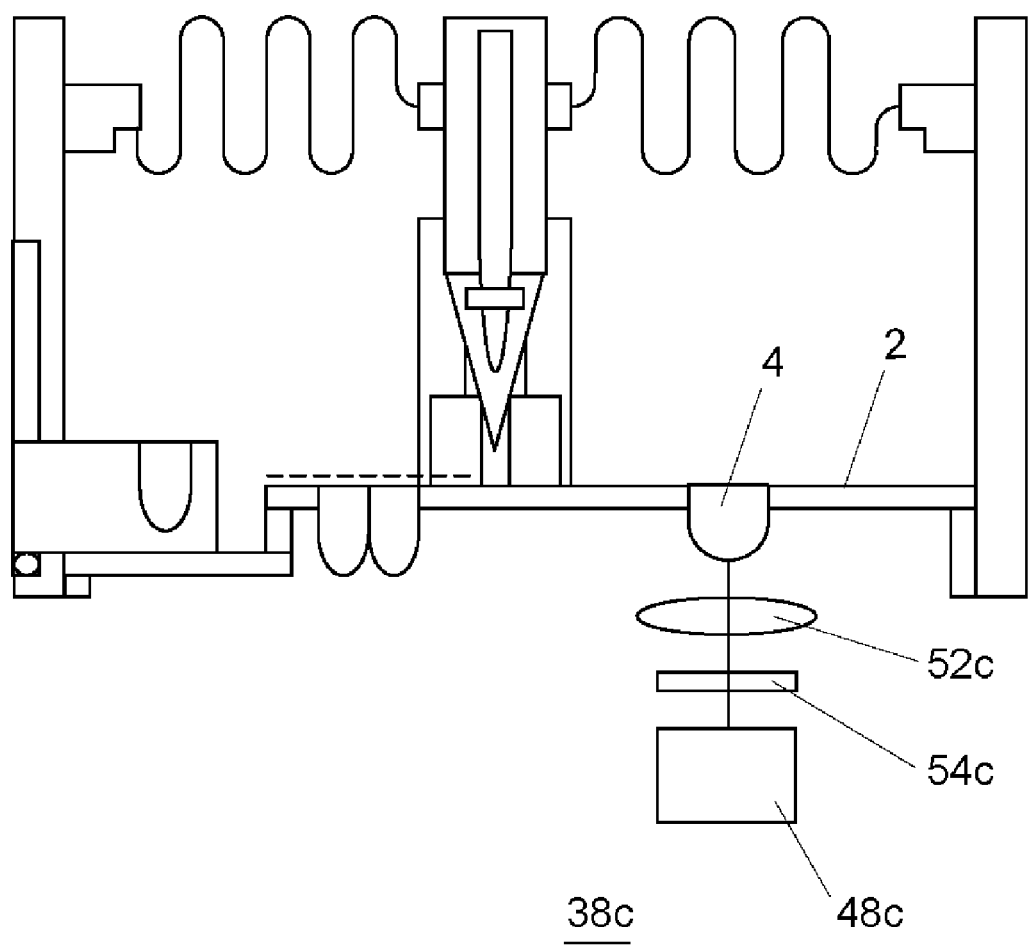
FIG. 11 is a vertical sectional view showing a third embodiment of the detection unit used for the detection of a reaction product in the reaction kit of the present invention.

FIGS. 9 to 11 show examples of a detection unit to detect a reaction product in the reaction container in the reaction kit according to the present invention.

FIG. 9 shows an example of the detection unit including an absorbance detector. In this case, the reaction container 4 preferably has a pair of parallel flat surfaces serving as a light incident surface through which measuring light enters and a light exiting surface through which measuring light exits. The detection unit 38a includes an irradiation optical system. The irradiation optical system has, on its optical path, a light source 40a, a pair of lenses 42a for once condensing light emitted from the light source 40a to obtain parallel light and then condensing the parallel light to irradiate the reaction container 4 with condensed light, a filter 44a arranged between the pair of lenses 42a at a position where the parallel light travels to select light having a predetermined wavelength from light emitted from the light source 40a to obtain measuring light, and mirrors 46 for guiding the measuring light to the light incident surface of the reaction container 4. As the light source 40a, a lamp light source such as a tungsten lamp which emits light having wavelengths ranging from the ultraviolet light region to the visible light region, a light-emitting diode (LED), a laser diode (LD), or the like is used. Further, the detection unit 38a includes a light-receiving optical system. The light-receiving optical system has, on its optical path, a photodetector 48a, mirrors 50 for guiding light exiting from the reaction container 4 through its light exiting surface to the photodetector 48a, a pair of lenses 52 for once converting the light into parallel light and then condensing the parallel light to introduce condensed light into the photodetector 48a, and a filter 54a arranged between the pair of lenses 52 at a portion where the parallel light travels to select light having a predetermined wavelength suitable for measurement. The reason for once converting light into parallel light by the lenses 42a and 52a is to improve the precision of wavelength selection by the filters 44a and 54a.

In the case of using such a detection unit 38a, light having a wavelength suitable for detecting a reaction product is selected from light emitted from the light source 40a by the filters 44a and 54a, and absorbance is measured at the selected wavelength to detect the reaction product.

FIG. 10 shows an example of a detection unit including a fluorescence detector. The detection unit 38b includes an excitation optical system. The excitation optical system has a light source 40b, a pair of lenses 42b for once condensing light emitted from the light source 40b to obtain parallel light and then condensing the parallel light to irradiate the reaction container 4 with condensed light, and a filter 44b arranged on the optical path of parallel light beams obtained by the lens 42b to select light having a predetermined excitation wavelength from light emitted from the light source 40b. Further, the detection unit 38b includes a light-receiving optical system. The light-receiving optical system has a photodetector 48b, a pair of lenses 52b for receiving fluorescence emitted from the reaction container 4, once converting the fluorescence into parallel light and condensing the parallel light to introduce condensed light into the photodetector 48b, and a filter 54b arranged on the optical path of the parallel fluorescence beams obtained by the lens 52b to select light having a predetermined fluorescence wavelength. Similarly, the reason for once converting light into parallel light by the lenses 42b and 52b is to improve the precision of wavelength selection by the filters 44b and 54b.

In the case of using such a detection unit 38b, light having an excitation wavelength for exciting a reaction product is selected from light emitted from the light source 40b by the filter 44b to irradiate the reaction product contained in the reaction container 4 with the selected light, and fluorescence emitted from the reaction product is received by the light-receiving optical system. Light having a predetermined fluorescence wavelength is selected by the filter 54b, and the selected fluorescence is detected by the photodetector 48b.

FIG. 11 shows an example of the detection unit for detecting chemiluminescence or bioluminescence emitted from a reaction product. The detection unit 38c has a photodetector 48c for detecting light emitted from the reaction container 4, a lens 52c for receiving light emitted from the reaction container 4 and guiding condensed light to the photodetector 48c, and a filter 54c for selecting light having a predetermined emission wavelength from the condensed light.

In the case of using such a detection unit 38c, chemiluminescence or bioluminescence emitted from a reaction product contained in the reaction container 4 is condensed by the lens 52c. Light having a predetermined emission wavelength is selected by the filter 54c, and the selected light is detected by the photodetector 48c.

FIGS. 12 to 16 show other embodiments different in the structure of the reaction plate. The reaction plate of the embodiments described above is designed to allow a reaction product to be detected in the reaction container 4, but the reaction plate of each of the reaction kits shown in FIGS. 12 to 16 further has an analysis section for analyzing a reaction product.

Figure 12A:
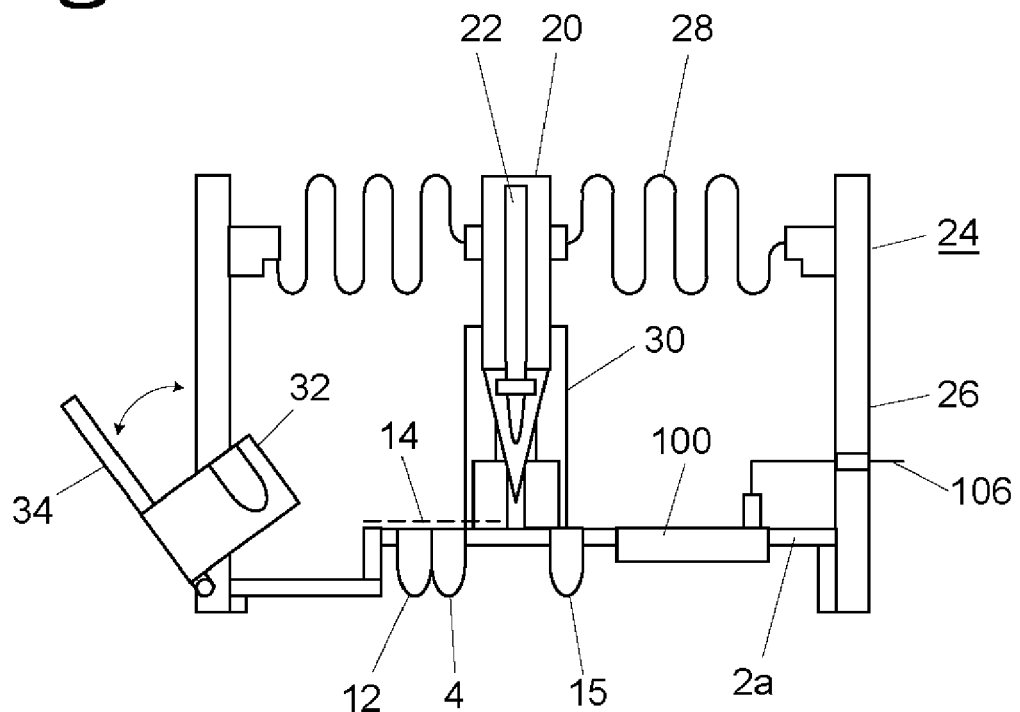
FIG. 12A is a vertical sectional view of another embodiment of a reaction kit.
Figure 12B:
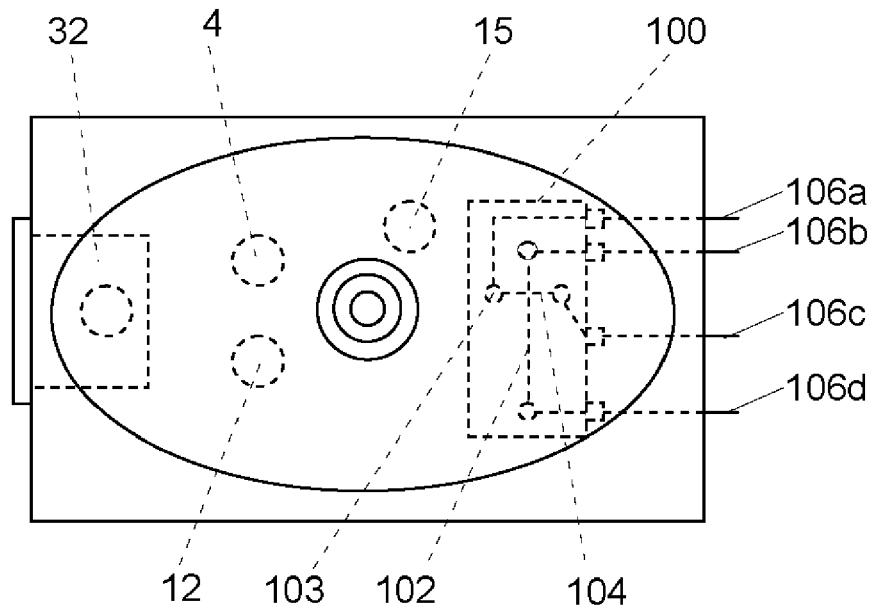
FIG. 12B is a plan view showing a reaction plate and a dispensation tip in the embodiment.

A reaction plate 2a of the embodiment shown in FIGS. 12A and 12B has an electrophoresis section as the analysis section. In this case, an electrophoresis chip 100 is used as one example of the electrophoresis section. The electrophoresis chip 100 has a reaction product injection section 103, an electrophoretic separation channel 102, and electrodes 106a to 106d for applying an electrophoresis voltage. The electrophoresis chip 100 further has, in addition to the electrophoretic separation channel 102, a sample introduction channel 104 arranged so as to cross the channel 102 to introduce a sample into the channel 102, but the sample introduction channel 104 may have such a structure that a sample can be directly introduced thereinto from one end of the channel 102. The electrophoresis chip 100 is subjected to fluorescence detection from the back surface side thereof, and is therefore made of a low self-fluorescence and an optically-transparent resin such as polycarbonate, glass, or quartz.

The reaction plate 2a further has a separation buffer container 15 provided in the top surface thereof to receive a separation buffer to be injected into the channels 102 and 104. The separation buffer container 15 is sealed with a film through which the tip of the dispensation tip 20 can pass.

The electrodes 106a to 106d for applying an electrophoresis voltage are connected to both ends of the channel 102 and 104, respectively. These electrodes 106a to 106d are extended to the outside of the cover 24 so as to be connected to a power supply provided outside the reaction kit. Each of the channels 102 and 104 has a reservoir at its end, and a separation buffer contained in the separation buffer container 15 is injected into the reservoirs.

In a case where the embodiment is used for gene analysis, the reagent container 12 is allowed to previously contain a PCR reaction reagent. In this case, the reaction container 4 serves as a PCR reaction container. In a case where a gene sample is measured using the embodiment, a sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered over a mixture of the sample and the reagent contained in the reaction container 4, and then PCR reaction is carried out by controlling the temperature of the reaction mixture contained in the reaction container 4 according to a predetermined temperature cycle. A separation buffer is supplied by the dispensation tip 20 from the separation buffer container 15 to the channels 102 and 104 through the reservoirs in the electrophoresis chip 100.

After the completion of the PCR reaction, an obtained reaction mixture is supplied as a sample by the dispensation tip 20 from the reaction container 4 to the injection section 103 of the electrophoresis chip 100 having the separation buffer previously supplied. Then, a voltage is applied from a power supply 101 (see FIG. 13) provided in the reaction kit treatment equipment to the channels 102 and 104 through the electrodes 106a to 106d to introduce the sample into the electrophoretic separation channel 102, and then the sample is electrophoresed in the channel 102 to be separated into its components. In order to detect sample components separated by electrophoresis, the reaction kit treatment equipment has a detection unit 38d. It is to be noted that in this case, the reaction container 4 is used as a PCR reaction container, but a PCR reaction container may be provided separately from the reaction container 4.

Figure 13:
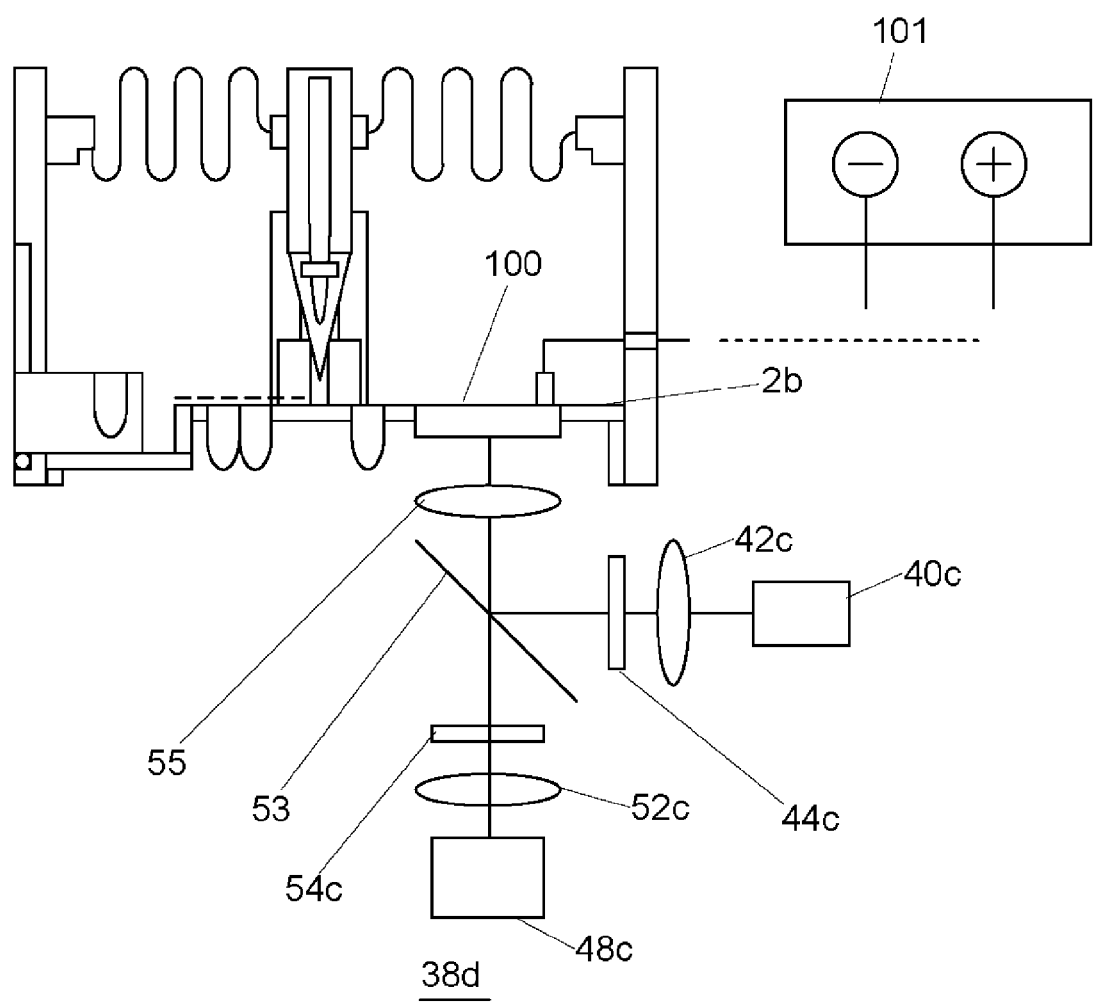
FIG. 13 is a vertical sectional view showing an example of a detection unit used for the detection of a reaction product in the reaction kit of the embodiment, together with the reaction kit.

The detection unit 38d is shown in FIG. 13. The detection unit 38d includes an excitation optical system and a fluorescence-receiving optical system to carry out fluorescence detection of sample components passing through a predetermined position in the electrophoretic separation channel 102. Since the detection unit 38d detects the fluorescence of sample components passing through a fixed position, it is not necessary to move the detection unit 38d.

The excitation optical system has a light source 40c, a lens 42c for condensing light emitted from the light source 40c to obtain parallel light, and a filter 44c provided on the optical path of parallel light beams obtained by the lens 42c to select light having a predetermined excitation wavelength from light emitted from the light source 40c.

The detection unit 38d further includes a dichroic mirror 53 and an objective lens 55 to irradiate a predetermined position in the electrophoretic separation channel 102 with excitation light obtained by the excitation optical system from the back surface side of the electrophoresis chip 100 and to receive fluorescence emitted from the position and convert it into parallel light. It is to be noted that the dichroic mirror 53 is designed so as to reflect light having an excitation wavelength to be used for the embodiment and transmit light having a fluorescence wavelength.

The fluorescence-receiving optical system of the detection unit 38d is arranged at a position where it can receive fluorescence converted into parallel light by the objective lens 55 and passed through the dichroic mirror 53. The fluorescence-receiving optical system has a filter 54c for selecting light having a predetermined fluorescence wavelength from fluorescence passed through the dichroic mirror 53 and a lens 52c for condensing the fluorescence having a wavelength selected by the filter 54c to introduce condensed light into a detector 48c. As described above, the reason for once converting light into parallel light by the lenses 42c and 55 is to improve the precision of wavelength selection by the filters 44c and 54c.

In the case of using such a detection unit 38d, light having an excitation wavelength for exciting a reaction product is selected by the filter 44c from light emitted from the light source 40c to irradiate the reaction product passing through a predetermined position in the electrophoretic separation channel 102 with the light, and fluorescence emitted from the reaction product is received by the light-receiving optical system, and light having a predetermined fluorescence wavelength is selected by the filter 54c and detected by the photodetector 48c.

Figure 14A:
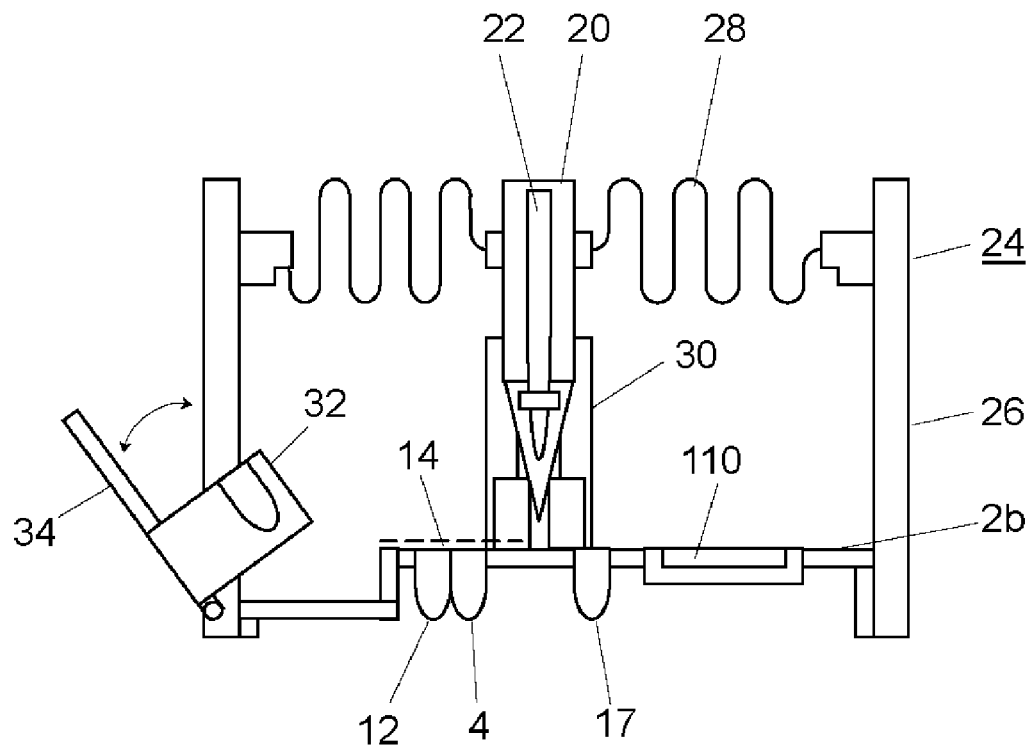
FIG. 14A is a vertical sectional view of still another embodiment of a reaction kit.
Figure 14B:
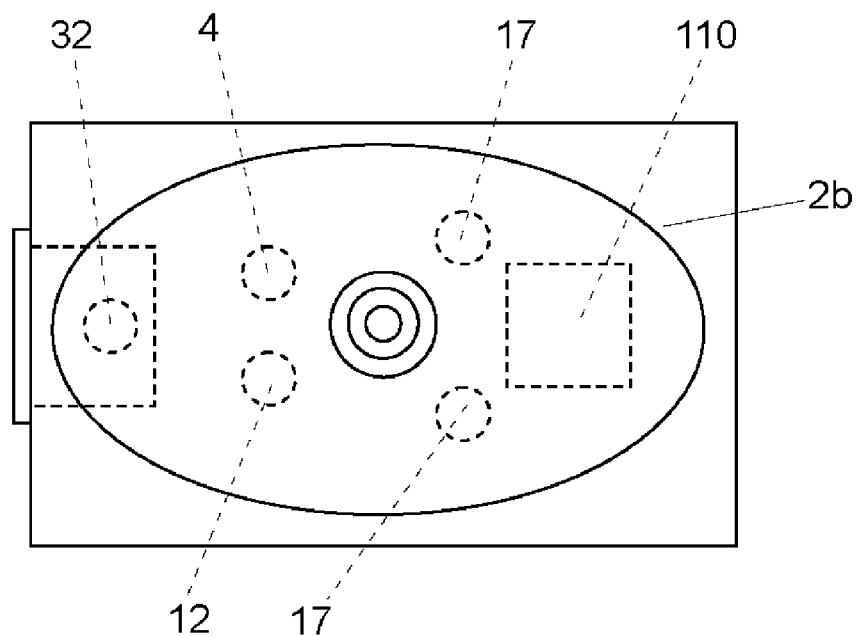
FIG. 14B is a plan view showing a reaction plate and a dispensation tip in the embodiment.

A reaction plate 2b of the embodiment shown in FIGS. 14A and 14B has a DNA chip 110 as the analysis section. When a reaction product contains a gene, probes, which react with the gene, are immobilized to the DNA chip 110. The DNA chip 110 is subjected to fluorescence detection from the back surface side thereof, and is therefore made of a low self-fluorescence and an optically-transparent resin such as polycarbonate or glass.

The reaction plate 2a further has cleaning solution containers 17 formed in the top surface thereof. The cleaning solution containers 17 contain a cleaning solution for separating and removing the reaction product not having been bound to the probes from the reaction product having been bound to the probes in the DNA chip 110. Further, the cleaning solution containers 17 are sealed with a film through which the tip of the dispensation tip 20 can pass.

In a case where the embodiment is used for gene analysis, the reagent container 12 is allowed to previously contain a PCR reaction reagent. In this case, the reaction container 4 serves as a PCR reaction container. In a case where a gene sample is measured using the embodiment, the sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered onto a mixture of the sample and the reagent contained in the reaction container 4, and then PCR reaction is carried out by controlling the temperature of the mixture contained in the reaction container 4 according to a predetermined temperature cycle.

After the completion of the PCR reaction, an obtained reaction mixture is supplied as a sample from the reaction container 4 to the DNA chip 110 by the dispensation tip 20. After the completion of incubation, a cleaning solution is supplied from the cleaning solution container 17 to the DNA chip 110 by the dispensation tip 20, and then a reaction product not having been bound to the probes is removed by sucking the cleaning solution into the dispensation tip 20.

The reaction product having been bound to the probes can be detected by fluorescence by previously labeling the reaction product with a fluorescent material. The detection of the presence of fluorescence in the DNA chip 110 indicates that a gene corresponding to the probe immobilized at a position where fluorescence has been detected is contained in the sample. In order to detect the reaction product having been bound to the probes in the DNA chip 110, the reaction kit treatment equipment includes a detection unit 38e.

Figure 15:
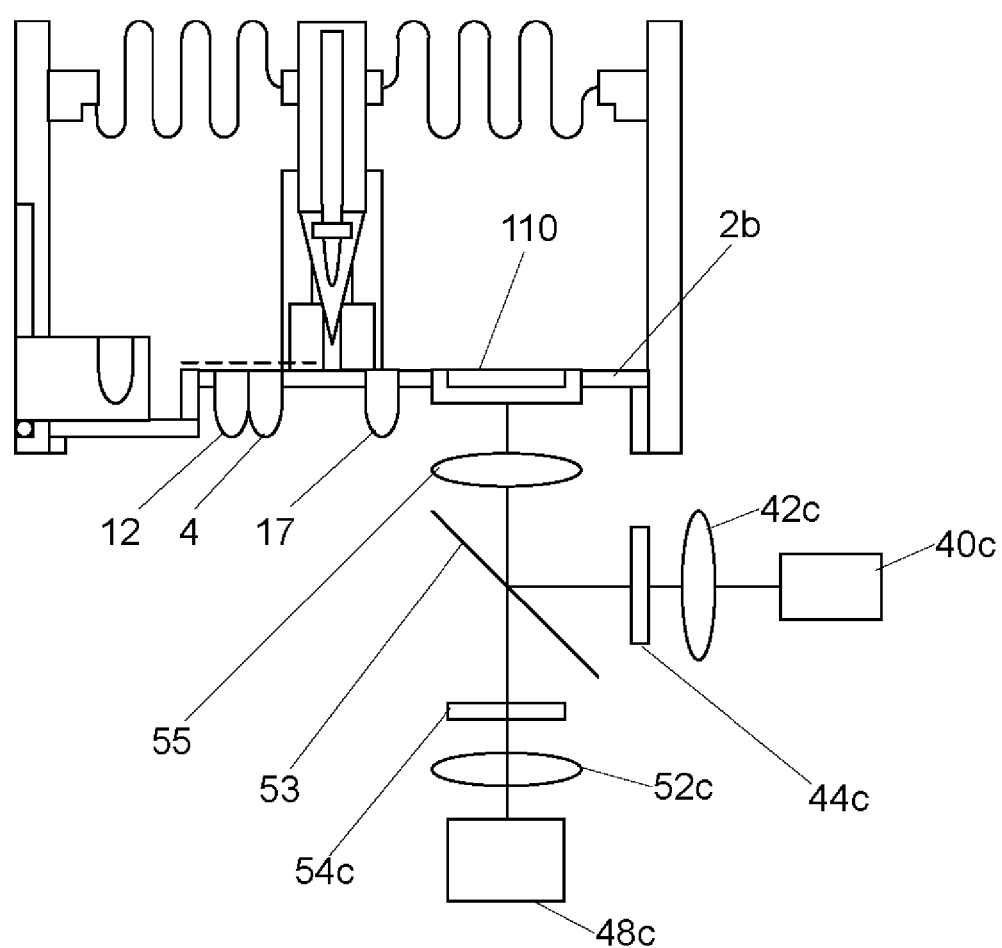
FIG. 15 is a vertical sectional view showing an example of a detection unit used for the detection of a reaction product in the reaction kit of the embodiment, together with the reaction kit.
Figure 22:
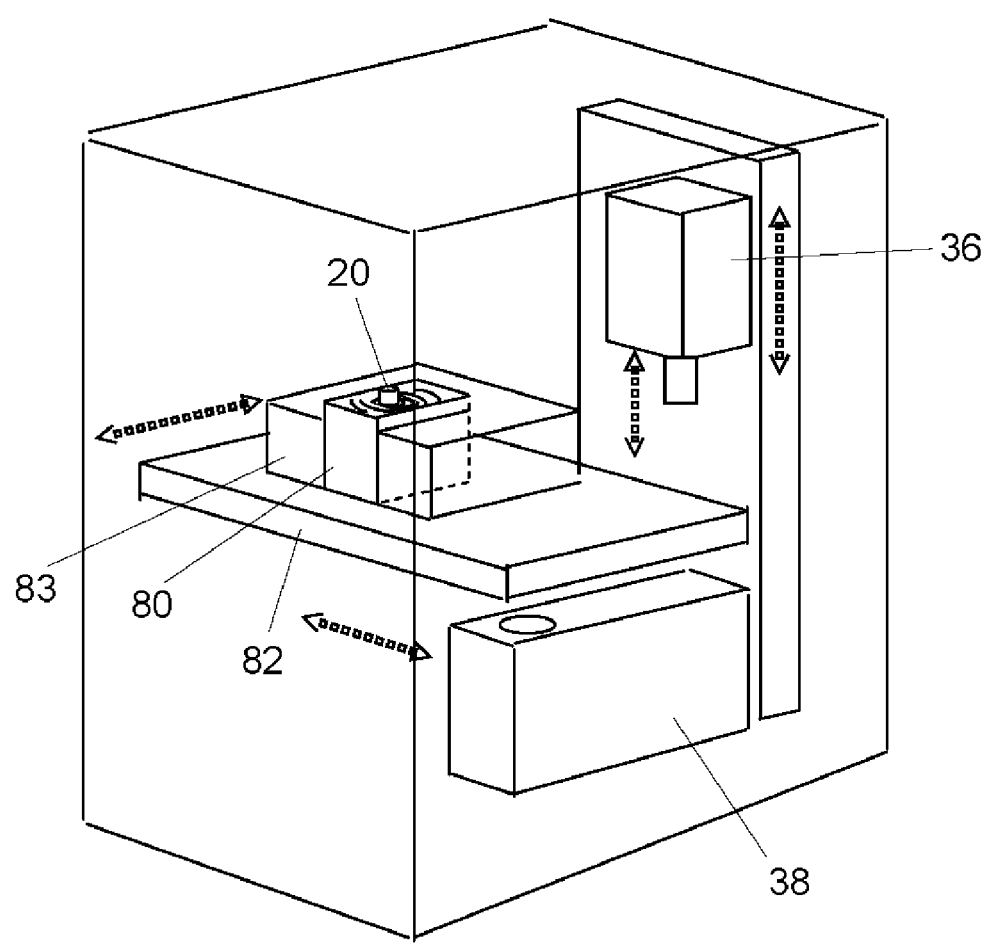
FIG. 22 is a schematic perspective view showing one example of an inside of reaction kit treatment equipment.

The detection unit 38e is shown in FIG. 15. The structure of an optical system of the detection unit 38e is the same as that of the detection unit 38d shown in FIG. 13, and therefore the description thereof is omitted. The detection unit 38e is different from the detection unit 38d shown in FIG. 13 in that it is movably supported so that fluorescence detection can be carried out for all the probes arranged in the DNA chip 110. Such detection can be achieved, as shown in FIG. 22, by allowing a table 82 to move in the X direction and by allowing the detection unit 38e to move in the Y direction.

Figure 16:
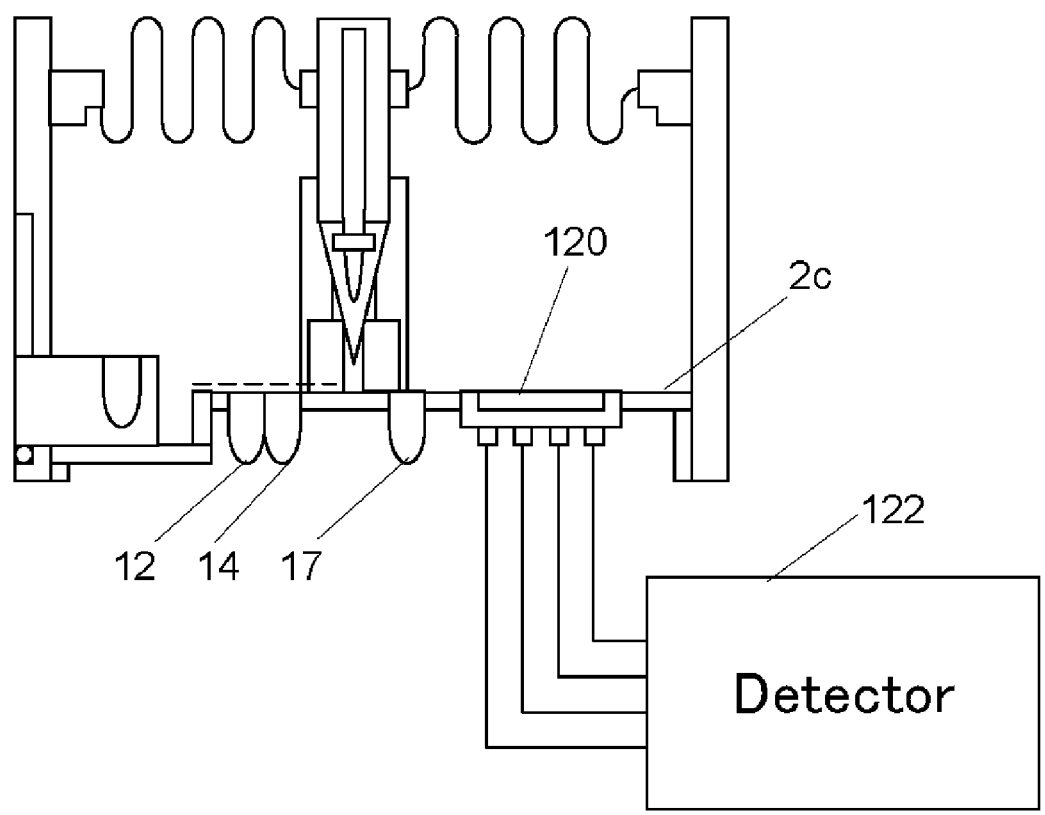
FIG. 16 is a vertical sectional view showing still another embodiment of the reaction kit, together with an example of a detection unit used for the detection of a reaction product.

A reaction plate 2c of the embodiment shown in FIG. 16 has a DNA chip 120 as the analysis section. The DNA chip 120 is different from the DNA chip 110 of the embodiment shown in FIG. 14 in that it is designed to allow a reaction product to be detected not by fluorescence detection but by electric detection. The DNA chip 120 utilizes a phenomenon in which the current value of each probe varies depending on whether a sample gene has been bound to the probe or not. Since the DNA chip 120 is not subjected to optical detection, the material of the DNA chip 120 does not need to be optically transparent but needs to be electrically insulating.

When a reaction product contains a gene, probes, which react with the gene, are immobilized to the DNA chip 120. Each of the probes is connected to an electrode provided on the back surface of the reaction plate so that the current value thereof can be measured. In the case of using the reaction kit, it is not necessary to previously label a sample with a fluorescent material.

The electrodes provided on the back surface of the reaction plate and connected to the probes are connected to a detector 122 provided in the reaction kit treatment equipment to measure the current value of each of the probes to detect the reaction product in the DNA chip 120.

The reaction plate 2c also has a cleaning solution container 17 formed in the top surface thereof. The cleaning solution container 17 contains a cleaning solution for separating the reaction product not having been bound to the probes immobilized to the DNA chip 120 from the reaction product having been bound to the probes and removing the former from the DNA chip 120. Further, the cleaning solution container 17 is sealed with a film through which the tip of the dispensation tip 20 can pass. The reagent container 12 previously contains a PCR reaction reagent. The reaction container 4 serves as a PCR reaction container.

In a case where a gene sample is measured by the reaction kit of the embodiment, the sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered onto a mixture of the sample and the reagent contained in the reaction container 4, and then PCR reaction is performed by controlling the temperature of the mixture contained in the reaction container 4 according to a predetermined temperature cycle.

After the completion of the PCR reaction, an obtained reaction mixture is supplied as a sample from the reaction container 4 to the DNA chip 120 by the dispensation tip 20. Then, a cleaning solution is supplied from the cleaning solution container 17 to the DNA chip 120 by the dispensation tip 20, and then a reaction product not having been bound to the probes is removed by sucking the cleaning solution into the dispensation tip 20.

In order to detect the reaction product having been bound to the probes in the DNA chip 110, the reaction kit treatment equipment includes a detector 122. After the reaction product not having been bound to the probes is removed, the current value of each probe is measured by the detector 122.

It is to be noted that a gene sample can be measured even when the DNA chip 110 or 120 of the reaction kit shown in FIG. 12 or 14 is replaced with a hybridization region.

Figure 17:
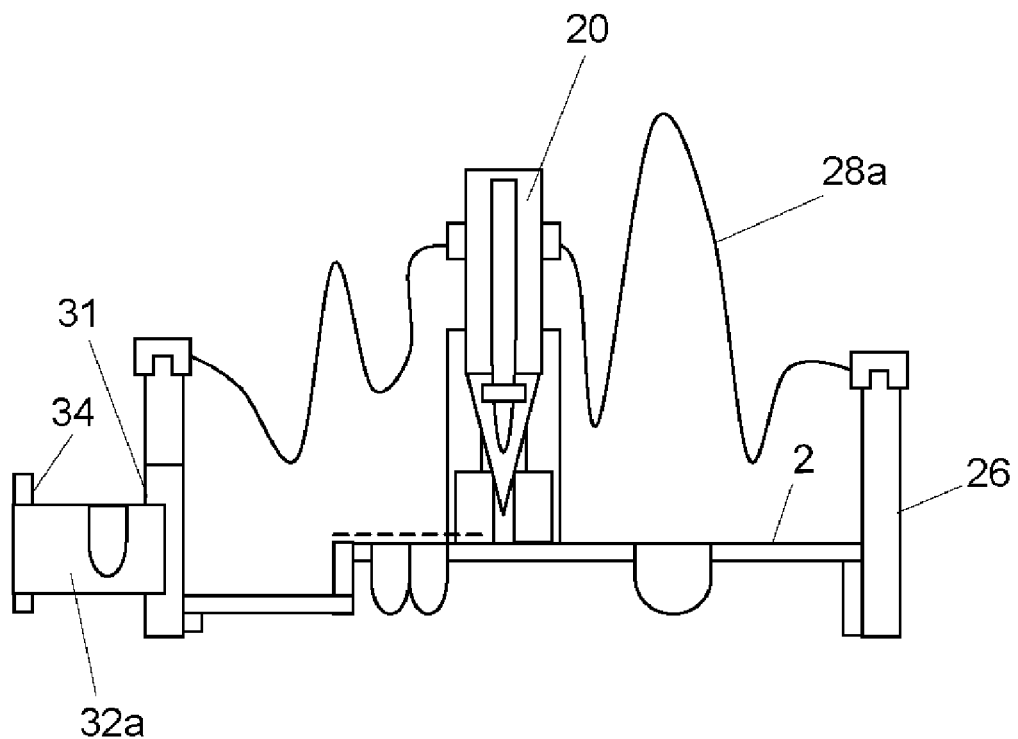
FIG. 17 is a vertical sectional view showing still another embodiment of the reaction kit.

FIG. 17 shows another reaction kit different in the structure of the cover. More specifically, the reaction kit shown in FIG. 1 has a bellows film 28 as part of the cover movably supporting the dispensation tip 20 and covering a space above the reaction plate 2, but the embodiment shown in FIG. 17 has a flexibly deformable film 28a as part of the cover. As in the case of the bellows film 28, the film 28a is preferably made of Nylon®, polyvinyl chloride, or a rubber material such as silicone rubber.

Further, the embodiment shown in FIG. 17 is different from the embodiment shown in FIG. 1 also in the structure of the sample container. More specifically, in the case of the reaction kit shown in FIG. 1, one side of the sample container is rotatably supported by the cover main body 26, but a sample container 32a of the reaction kit shown in FIG. 15 is slidably attached to the cover main body 26. Also, in the case of such a sample container 32a, a sample can be dispensed into the sample container 32a by pulling the sample container 32a toward the outside of the cover main body 26. The sample container 32a of the embodiment shown in FIG. 17 is the same as the sample container 32 of the embodiment shown in FIG. 1 in that the opening 31 of the cover main body 26 can be closed by sliding the sample container 32a toward the inside of the cover main body 26 and can be sealed by bringing the plate 34 into intimate contact with the cover main body 26 using a pressure-sensitive adhesive previously applied onto the inner surface of the plate 34 or by using a sealant.

The detection unit 38a, 38b, or 38c is arranged in the reaction kit treatment equipment so as to be located under the reaction plate 2 of the reaction kit attached to the treatment equipment.

Figure 18A:
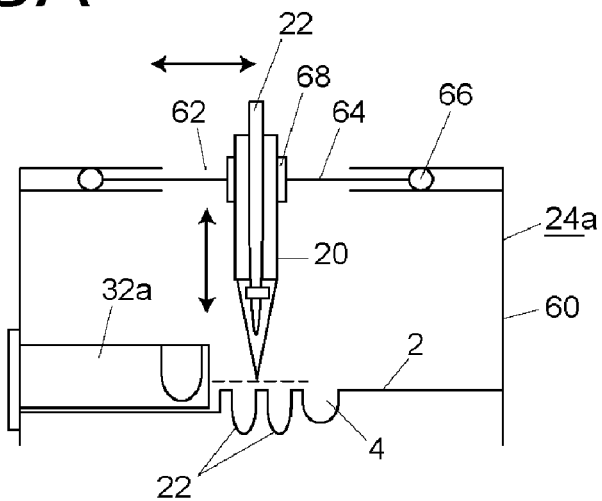
FIG. 18A is a vertical sectional view showing still another embodiment of the reaction kit.
Figure 18B:
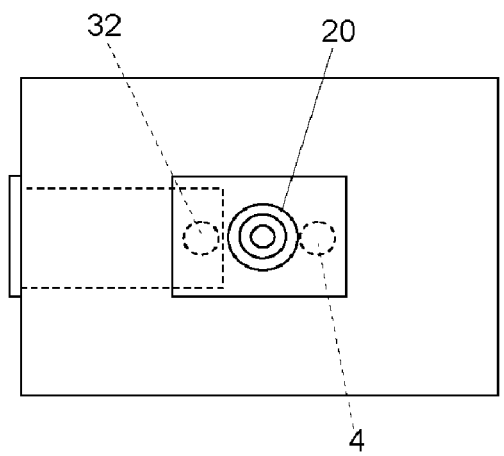
FIG. 18B is a plan view showing a reaction plate and a dispensation tip in the embodiment.
Figure 18C:
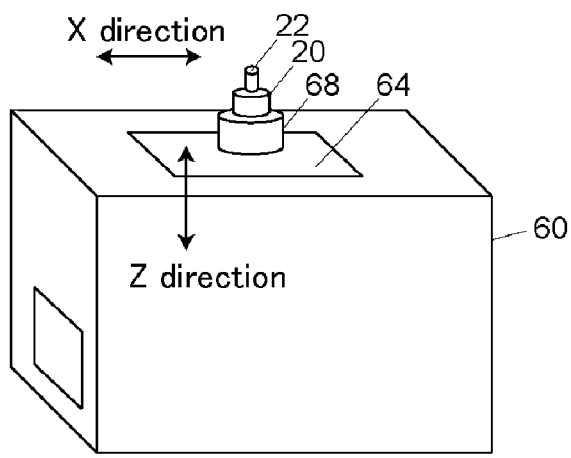
FIG. 18C is an outside perspective view of the embodiment.

FIGS. 18A to 18C show another embodiment, FIG. 18A is a vertical sectional view, FIG. 18B is a horizontal sectional view and FIG. 18C is a perspective view showing the appearance of the reaction kit. The embodiment shown in FIGS. 18A to 18C has a cover movably supporting the dispensation tip 20, and the cover is made of a material having stiffness. A cover main body 60 of a cover 24a has an opening 62 located above the reaction plate 2. In the opening 62, a cover plate 64 for movably supporting the dispensation tip 20 is provided so that the dispensation tip 20 can be moved within a range defined by the opening 62. A part of the cover main body 60 around the opening 62 has a double structure having an interior gap, and a sealant 66 is provided around the periphery of the cover plate 64. The sealant 66 is moved in the X direction in the interior gap of the double structure provided around the opening 62 of the cover main body 60, which allows the cover plate 64 to move in the X direction in a horizontal plane. Further, the dispensation tip 20 is supported by the cover plate 64 by means of another sealant 68, which is interposed between the dispensation tip 20 and the cover plate 64, so as to be able to slide in the vertical direction (Z direction).

In the embodiment shown in FIGS. 18A to 18C, the cover plate 64 is moved in a horizontal plane while the reaction kit is kept hermetically sealed by a sealing structure constituted from the cover plate 64, the sealant 66, and the interior gap of the double structure provided in the upper part of the cover main body 60, and the dispensation tip 20 is moved in the vertical direction while the reaction kit is kept hermetically sealed by the sealant 68. This makes it possible to freely move the dispensation tip 20 in a space above the reaction plate 2 in two directions, i.e., in the vertical direction and a direction in a horizontal plane.

Figure 19A:
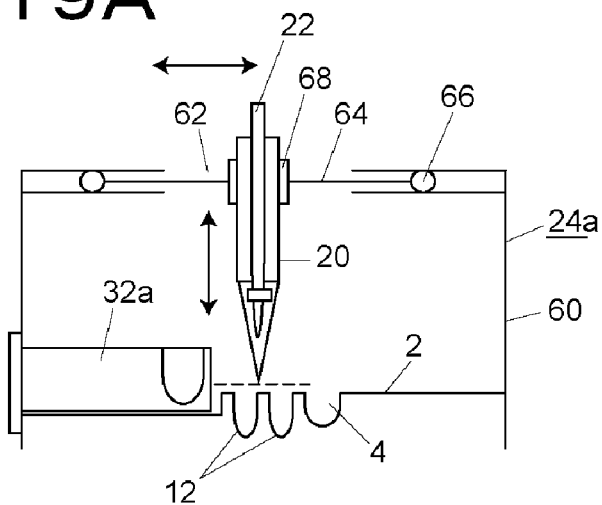
FIG. 19A is a vertical sectional view showing still another embodiment of the reaction kit.
Figure 19B:
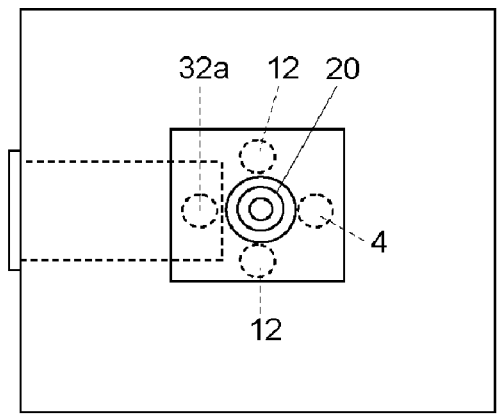
FIG. 19B is a plan view showing a reaction plate and a dispensation tip in the embodiment.
Figure 19C:
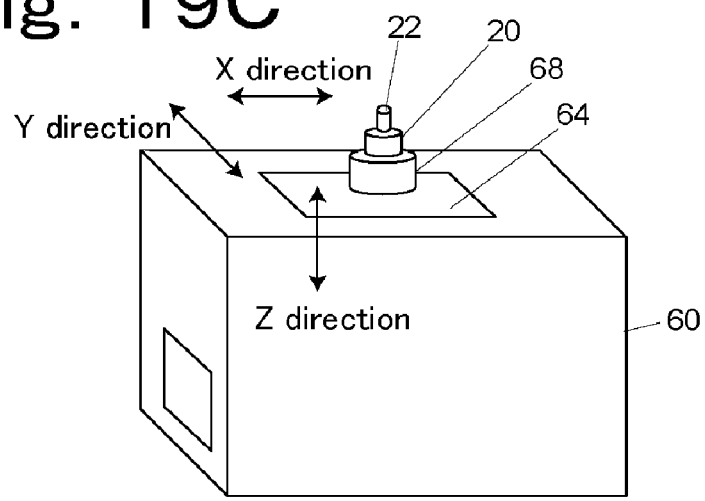
FIG. 19C is an outside perspective view of the embodiment.

FIGS. 19A to 19C show another embodiment. The embodiment shown in FIGS. 19A to 19C is the same as the embodiment shown in FIGS. 18A to 18C except that the cover plate 64 can be moved in two directions, i.e., X and Y directions, and that the number of the reagent containers 12 provided in the reaction plate 2 is increased.

Figure 20A:
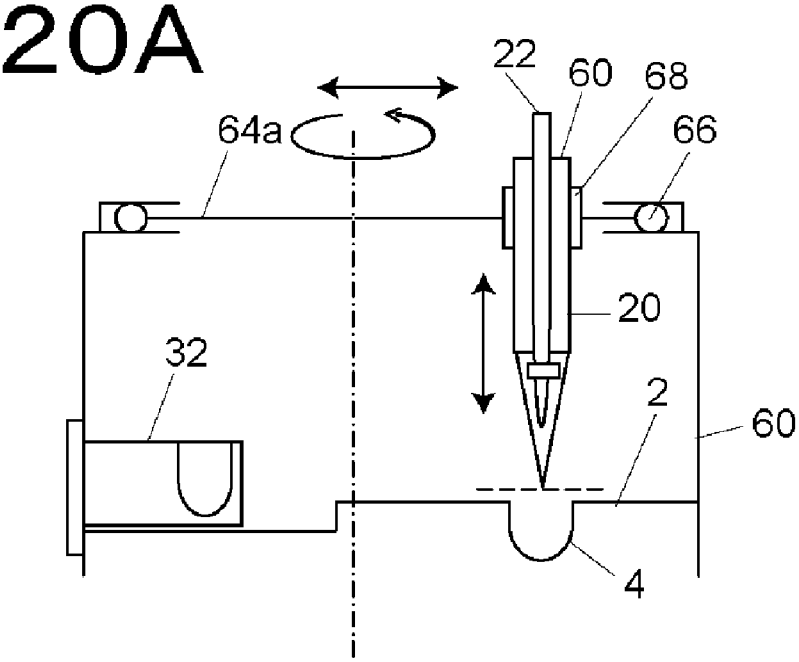
FIG. 20A is a vertical sectional view showing still another embodiment of the reaction kit.
Figure 20B:
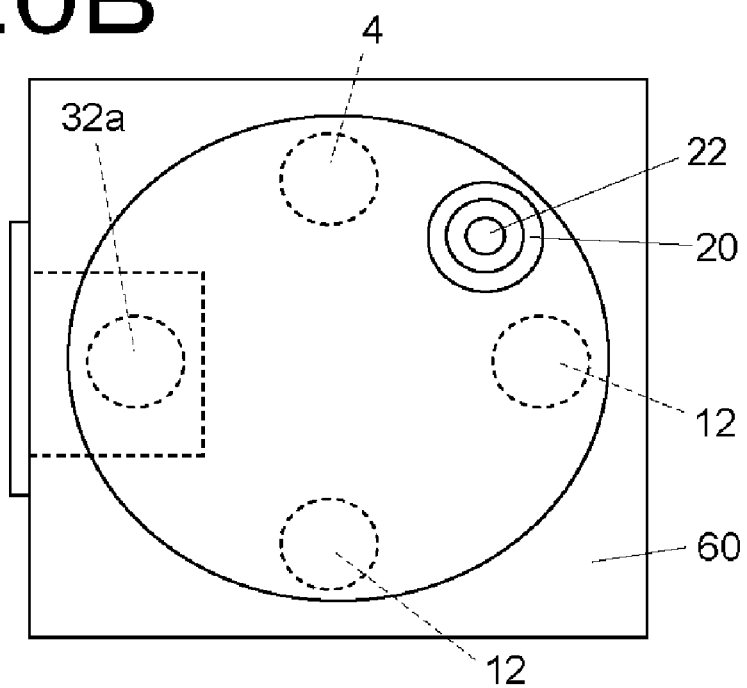
FIG. 20B is a plan view showing a reaction plate and a dispensation tip in the embodiment.

FIGS. 20A and 20B show another embodiment. The embodiment shown in FIGS. 20A and 20B is different from the embodiment shown in FIGS. 18A to 18C in that a cover plate 64a as an upper member of the cover is supported so as to be able to rotate in the in-plane direction to move the dispensation tip 20 in the in-plane direction. The cover plate 64a has a disc shape, and the sealant 66 is attached to the periphery of the cover plate 64a. The sealant 66 is held in the interior gap of the double structure provided in the upper part of the cover main body 60, and rotatably supports the cover plate 64a while keeping the reaction kit hermetically sealed. The dispensation tip 20 is supported by the cover plate 64a by means of the sealant 68 so as to be able to move in the vertical direction. The dispensation tip 20 supported by the cover plate 64a is located off the center of rotation of the cover plate 64a.

By rotating the cover plate 64a, it is possible to move the dispensation tip 20 on the circumference of a circle whose center is the rotational center of the cover plate 64a. Therefore, the reaction container 4 and the reagent containers 12 provided in the reaction plate 2 and the sample container 32 are arranged so as to be located on the movement locus of the dispensation tip 20.

Figure 21A:
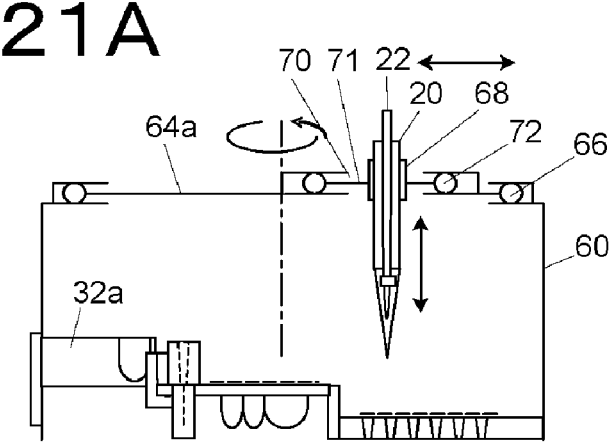
FIG. 21A is a vertical sectional view showing still another embodiment of the reaction kit.
Figure 21B:
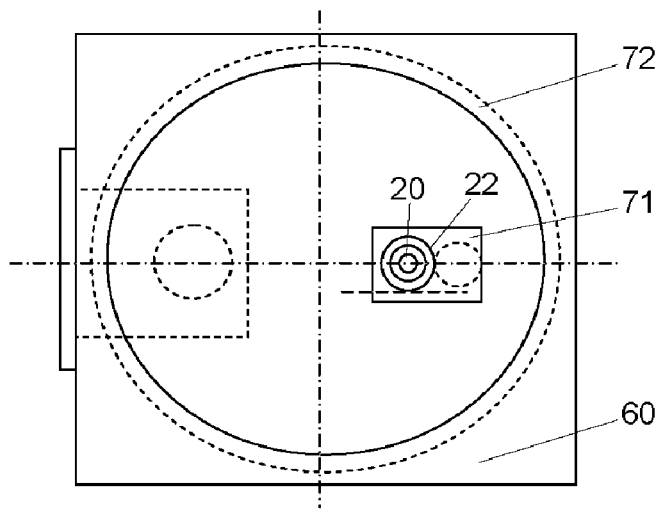
FIG. 21B is a plan view showing a reaction plate and a dispensation tip in the embodiment.
Figure 21C:
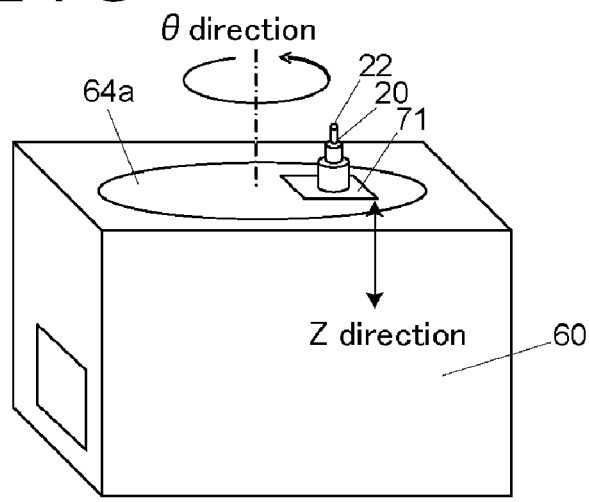
FIG. 21C is an outside perspective view of the embodiment.

FIGS. 21A to 21C show still another embodiment. The reaction kit shown in FIGS. 21A to 21C is different from the reaction kit shown in FIGS. 20A and 20B in that the cover plate 64a also has an opening 70, a double structure having an interior gap is provided around the opening 70, and another cover plate 71 is movably supported by the double structure by means of a sealant 72 held in the interior gap of the double structure. The dispensation tip 20 is supported by the cover plate 71 by means of another sealant 68 so as to be able to move in the vertical direction.

The dispensation tip 20 can also be moved in the in-plane direction by the sealant 72. Therefore, the dispensation tip 20 can be moved within a range defined by both the circumference of a circle obtained by rotating the cover plate 64a and a horizontal plane obtained by moving the smaller cover plate 71 movable by the sealant 72, that is, within a doughnut-shaped range whose center is the rotational center of the cover plate 64a. In the case of the reaction kit shown in FIG. 19, the moving range of the dispensation tip 20 becomes larger, and therefore it is possible to increase the numbers of the reaction containers 4 and the reagent containers 12 arranged in the moving range of the dispensation tip 20. In addition, it is also possible to increase the degree of freedom of arrangement of these containers and the sample container 32.

FIG. 22 is a perspective view schematically showing the interior structure of one embodiment of the treatment equipment for treating the reaction kits according to the present invention. The reference numeral 80 denotes the reaction kit described above. The reaction kit 80 is attached onto a table 82 provided as a reaction kit attachment section. The table 82 has an opening in its surface facing the lower surface of the reaction kit 80. Under the table 82, a detection unit 38 is arranged to optically detect a reaction product contained in the reaction container 4 of the reaction kit 80. On the table 82, a temperature control unit 83 is arranged to control the temperature of the reaction kit 80. In a case where gene amplification reaction is carried out in the reaction container 4 or a reaction container for gene amplification provided separately from the reaction container 4 of the reaction kit, the temperature control unit 83 is used to carry out temperature control for gene amplification reaction. Further, in a case where the reaction kit has an analysis section requiring temperature control, the temperature control unit 83 is used to carry out temperature control of the analysis section. The temperature control unit 83 may have both the function of carrying out temperature control for gene amplification reaction and the function of carrying out temperature control of the analysis section. The detection unit 38 generically denotes the detection means shown in FIGS. 9 to 11. The table 82 is moved in a forward-backward direction (X direction), and the detection unit 38 is supported so as to be able to move in a lateral direction (Y direction) orthogonal to the moving direction of the table 82.

The drive unit 36 for driving the dispensation tip 20 is attached near the table 82 so as to be able to move in the Y and Z directions. As shown in FIG. 3, the drive unit 36 has a tip holding section (a tip holder 36a) for holding the dispensation tip 20 by engaging with the proximal end of the dispensation tip 20 and a plunger holder 36b for driving the plunger 22 by engaging with the plunger 22 of the syringe provided in the dispensation tip 20. The tip holding section 36a and the plunger holder 36b are coaxially provided in the drive unit 36. Such a drive unit 36 allows both the movement of the dispensation tip 20 and the driving of the plunger 22 to be carried out.

Figure 23:
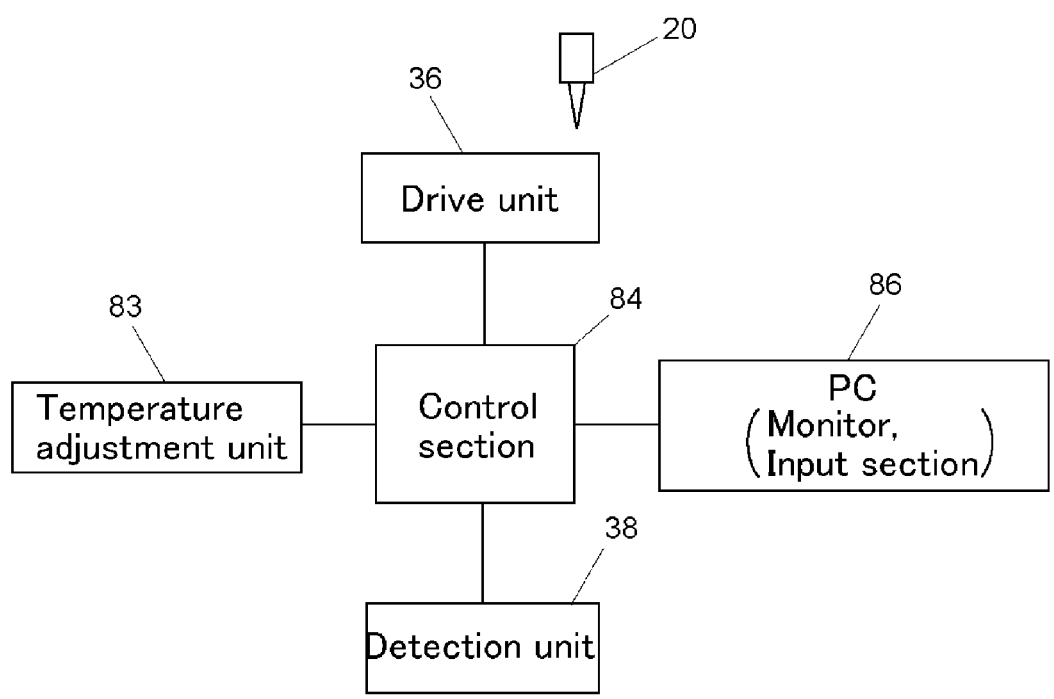
FIG. 23 is a block diagram that shows a control system of the reaction kit treatment equipment.

FIG. 23 is a block diagram showing the control system of the reaction kit treatment equipment according to the embodiment. The reaction kit treatment equipment includes a control section 84 for controlling the treatment of the reaction kit 80 attached to the table 82. The control section 84 is constituted from a dedicated purpose computer (CPU) or a general-purpose personal computer. The control section 84 controls the movement of the dispensation tip 20 driven by the drive unit 36 engaged with the proximal end of the dispensation tip 20, dispensation operation by the dispensation tip 20, temperature control carried out by the temperature control unit 83, and the operation of the detection unit 38 for optically detecting a reaction product by irradiating the reaction container 4 of the reaction kit 80 with measuring light or excitation light.

In order to use the control section 84 as an input section externally operated or a monitor for displaying detection results, an external computer such as a personal computer (PC) 86 may be connected to the control section 84.

INDUSTRIAL APPLICABILITY

The present invention can be applied to measurement of various chemical and biochemical reactions.

What is claimed is:
1. A reaction kit comprising:
a reaction plate having a reaction container placed on a surface side thereof for causing a sample to react;
a dispensation tip being placed above a surface side of the reaction plate, the dispensation tip comprising:
a dispensation nozzle attached to a distal end thereof,
a syringe being connected to a proximal end portion of the dispensation nozzle and having a hollow inner portion,
a plunger sliding in a cylinder of the dispensation nozzle for sucking and discharging liquid through the dispensation nozzle, and
a separation member being arranged inside of the cylinder and being placed between a proximal end portion of the plunger and a proximal end portion of the cylinder, the separation member comprising a member selected from the group consisting of a diaphragm and a film, and having airtightness so as to separate an inside of the nozzle from outside and flexibility so as to allow the plunger to slide therein; and
a cover for coveting a plate upper-space on the surface side of the reaction plate, the cover being provided integrally with the reaction plate so that the plate upper-space is cut off from the outside and including a bellows film formed from a flexible diaphragm or a flexible film, and the cover movably supporting the dispensation tip, with a distal end thereof being located inside the plate upper-space and a proximal end being located outside the plate upper-space by holding the dispensation tip undetachably by the bellows film.

2. The reaction kit according to claim 1, wherein the dispensation tip has an air hole communicating with a loop-shaped space formed by the cylinder, the plunger and the separation member, the air hole being provided separately from the dispensation nozzle and placed on an inside of the plate upper-space covered with the cover.

3. The reaction kit according to claim 1, further comprising a sample introducing section being used for injecting a sample into the plate upper-space from outside through an opening formed on one portion of the cover so as to be opened and closed.

4. The reaction kit according to claim 1, wherein the reaction plate further comprises a reagent container that houses a reagent to be used for a reaction of a sample, and is sealed with a film and placed on a surface side thereof.

5. The reaction kit according to claim 1, wherein the dispensation tip has a filter placed inside the distal end thereof.

6. The reaction kit according to claim 1, wherein the reaction plate comprises a gene amplification section on a front surface side thereof being used for carrying out a gene amplification reaction.

7. The reaction kit according to claim 1, wherein the reaction container is made of a light transmitting material so that optical measurements are carried out from a bottom portion thereof.

8. The reaction kit according to claim 1, wherein the reaction plate further comprises an analyzing section placed on the surface side thereof for analyzing a reaction product in the reaction container.

9. The reaction kit according to claim 8, wherein the analyzing section is an electrophoresis section for carrying out an electrophoretic separation on a reaction product.

10. The reaction kit according to claim 8, wherein the analyzing section is prepared as an area in which, when a gene is contained in a reaction product, probes to be reacted with the gene are arranged.

11. The reaction kit according to claim 1, wherein the cover movably supports the dispensation tip by using a material having airtightness and flexibility.

12. The reaction kit according to claim 1,
wherein the cover comprises a cover main body integrally formed with the reaction plate and a cover plate placed on an upper portion of the reaction plate on the surface side, the cover plate being supported hermetically by a sealant so as to slide within a horizontal plane relative to the cover main body, and
wherein the dispensation tip is supported hermetically by another sealant so as to slide in a vertical direction.

* * * * *